US012569494B2

(12) United States Patent
Dudakov et al.

(10) Patent No.: US 12,569,494 B2
(45) Date of Patent: Mar. 10, 2026

(54) COMPOSITIONS AND METHODS TO PROMOTE THYMIC REGENERATION

(71) Applicant: Fred Hutchinson Cancer Center, Seattle, WA (US)

(72) Inventors: Jarrod Dudakov, Seattle, WA (US); Sinead Kinsella, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 880 days.

(21) Appl. No.: 16/960,851

(22) PCT Filed: Jan. 11, 2019

(86) PCT No.: PCT/US2019/013349
§ 371 (c)(1),
(2) Date: Jul. 8, 2020

(87) PCT Pub. No.: WO2019/140300
PCT Pub. Date: Jul. 18, 2019

(65) Prior Publication Data

US 2021/0113573 A1 Apr. 22, 2021

Related U.S. Application Data

(60) Provisional application No. 62/616,252, filed on Jan. 11, 2018.

(51) Int. Cl.

| | |
|---|---|
| *A61K 31/5377* | (2006.01) |
| *A61K 31/12* | (2006.01) |
| *A61K 31/201* | (2006.01) |
| *A61K 31/202* | (2006.01) |
| *A61K 31/352* | (2006.01) |
| *A61K 31/365* | (2006.01) |
| *A61K 31/415* | (2006.01) |
| *A61K 31/4184* | (2006.01) |
| *A61K 31/426* | (2006.01) |
| *A61K 31/44* | (2006.01) |
| *A61K 31/4439* | (2006.01) |
| *A61K 31/47* | (2006.01) |
| *A61K 31/497* | (2006.01) |
| *A61K 31/5025* | (2006.01) |
| *A61K 31/505* | (2006.01) |
| *A61K 31/506* | (2006.01) |
| *A61K 31/52* | (2006.01) |
| *A61K 31/704* | (2006.01) |
| *A61K 31/7076* | (2006.01) |
| *A61K 38/10* | (2006.01) |
| *A61K 38/45* | (2006.01) |
| *C12N 15/113* | (2010.01) |

(52) U.S. Cl.
CPC .......... *A61K 31/5377* (2013.01); *A61K 31/12* (2013.01); *A61K 31/201* (2013.01); *A61K 31/202* (2013.01); *A61K 31/352* (2013.01); *A61K 31/365* (2013.01); *A61K 31/415* (2013.01); *A61K 31/4184* (2013.01); *A61K 31/426* (2013.01); *A61K 31/44* (2013.01); *A61K 31/4439* (2013.01); *A61K 31/47* (2013.01); *A61K 31/497* (2013.01); *A61K 31/5025* (2013.01); *A61K 31/505* (2013.01); *A61K 31/506* (2013.01); *A61K 31/52* (2013.01); *A61K 31/704* (2013.01); *A61K 31/7076* (2013.01); *A61K 38/10* (2013.01); *A61K 38/45* (2013.01); *C12N 15/113* (2013.01); *C12N 2310/113* (2013.01)

(58) Field of Classification Search
CPC .................................................. A61K 31/5377
See application file for complete search history.

(56) References Cited

U.S. PATENT DOCUMENTS

| | | | | |
|---|---|---|---|---|
| 8,383,124 | B2 * | 2/2013 | Zheng | A61K 45/06 514/885 |
| 9,119,824 | B2 * | 9/2015 | Dudakov | A61K 38/20 |
| 10,619,134 | B2 * | 4/2020 | Dudakov | C07K 14/005 |
| 2007/0155766 | A1 | 7/2007 | Zheng et al. | |
| 2009/0208953 | A1 | 8/2009 | Gutmann et al. | |
| 2016/0136244 | A1 | 5/2016 | Dudakov et al. | |
| 2017/0292111 | A1 | 10/2017 | Dudakov et al. | |
| 2023/0263800 | A1 * | 8/2023 | Dudakov | A61K 31/675 514/275 |

FOREIGN PATENT DOCUMENTS

| | | | |
|---|---|---|---|
| WO | WO2008154098 | A2 | 12/2008 |
| WO | WO2017143070 | A1 | 8/2017 |

OTHER PUBLICATIONS

Lin Y, Zheng Y. Approaches of targeting Rho GTPases in cancer drug discovery. Expert Opin Drug Discov. 2015;10(9):991-1010. doi: 10.1517/17460441.2015.1058775. Epub Jun. 18, 2015. (Year: 2015).*

(Continued)

*Primary Examiner* — Andrew D Kosar
*Assistant Examiner* — Gillian A Hutter
(74) *Attorney, Agent, or Firm* — C. Rachal Winger; Lee & Hayes PC

(57) ABSTRACT

Methods to promote thymic regeneration are described. The methods can inhibit nucleotide-binding oligomerization domain-containing protein 2 (NOD2), Rho GTPases, and/or microRNA 29c (miR29c). These inhibition methods can promote regenerative molecules, such as interleukin (IL)-22, IL-23, and/or bone morphogenetic protein 4 (BMP4). Promoting thymic regeneration can be beneficial in patients due to age, infection, or cancer therapies.

34 Claims, 14 Drawing Sheets

Specification includes a Sequence Listing.

(56) References Cited

OTHER PUBLICATIONS

Onesto et al., "Characterization of EHT 1864, a Novel Small Molecule Inhibitor of Rac Family Small GTPases", Methods of Enzymology, vol. 439, 2008 (Year: 2008).*
Gomez et al., "The GTPase Rac-1 Controls cell fate in the Thymus by diverting thymocyctes from Positive to Negative selection", Immunity, vol. 15, Nov. 2001 (Year: 2001).*
Dedakov et al., "Interleukin-22 drives endogenous thymic regeneration in mice", Science, Apr. 6, 2012 (Year: 2012).*
Ventevogel and Semproski, "Thymic Rejuenation and Age", Curr Opin Immunol. Aug. 2013 (Year: 2013).*
Chaundry et al., "Thymus: The Next (Re)Generation", Immunol Rev., May 2016 (Year: 2016).*
Jiang et al., "IL-22_CD4_ T-cells in patient with active systemic lupus erythematosus", Exp. Biol. Med, Feb. 2013 (Year: 2013).*
Zhao et al., "A soy diet accelerates renal damage in autoimmune MRL/Mp-lpr/lpr mice", International Immunopharmacology, Apr. 18, 2005 (Year: 2005).*
Bonnin et al., Secretion-mediated STAT3 activation promotes self-renewal of glioma stem-like cells during hypoxia. Oncogene 37, 1107-1118, Nov. 20, 2017 (Year: 2017).*
Xin et al., "Study on the relationship between DHA promoting NGF-induced PC12 differentiation and BMPs pathway", Sep. 30, 2014, National Natural Science Foundation of China (Year: 2014).*
Wertheimer et al., "Endothelial Cells promote Endogenous thymic regeneration after Injury Via BMP4 signaling", Blood, Dec. 6, 2014 (Year: 2014).*
Yoou et al., "Acteoside attenuates TSLP-induced mast cell proliferation via down-regulating MDM2", International Immunopharmacology, May 2015 (Year: 2015).*
Abreu et al., "Eicosatetraenoic Acid Enhances the effects of mesenchymal stromal cell therapy in Experimental Allergic Asthma", Front. Immunol. May 23, 2018 (Year: 2018).*
Deepthi et al., "Synthesis, DNA-binding, and cytotoxic studies on three copper(II) complexes of unsymmetrical analogues of curcumin", Journal of Coordination Chemistry, May 4, 2016 (Year: 2016).*
Ahn, et al., "MicroRNA transcriptome in the newborn mouse ovaries determined by massive parallel sequencing," Mol. Hum. Reprod., vol. 16, No. 7, 2010, pp. 463-471.
Allshire, "RNAi and Heterochromatin—a Hushed-Up Affair," Science, vol. 297, 2002, pp. 1818-1819.
Anastasiadis, et al., "Inhibition of RhoA by p120 catenin," Nat. Cell. Bio., vol. 2, 2000, pp. 637-644.
Belinsky, et al., "Multidrug resistance protein 4 protects bone marrow, thymus, spleen, and intestine from nucleotide analogue-induced damage," Cancer Res., vol. 67, No. 1, 2007, pp. 262-268.
Bennett, et al., "Evaluation of Cyclosporine-Treated Mice as Hosts for Growing and Testing the Chemosensitivity of First-Transplant-Generation Human Tumor Xenografts Implanted Under the Kidney Capsule," J. Natl. Cancer Inst., vol. 75, No. 5, 1985, pp. 925-936.
Bernstein, et al., "Role for a bidentate ribonuclease in the initiation step of RNA interference," Nature, vol. 409, 2001, pp. 363-366.
Boehm & Bleul, "Thymus-homing precursors and the thymic microenvironment," Trends in Immunology, vol. 27, No. 10, 2006, pp. 477-484.
Brown, et al., "The Rac and Rho hall of fame: a decade of hypertrophic signaling hits," Circ. Res., vol. 98, 2006, pp. 730-742.
Canning, et al., "Inflammatory Signaling by NOD-RIPK2 Is Inhibited by Clinically Relevant Type II Kinase Inhibitors," Chem. Biol., vol. 22, 2015, pp. 1174-1184.
Chiang, et al, "Mammilian microRNAs: experimental evaluation of novel and previously annotated genes," Genes and Development, vol. 24, 2010, pp. 992-1009.
Chinn & Markert, "Induction of tolerance to parental parathyroid grafts using allogeneic thymus tissue in patients with DiGeorge anomaly," J. Allergy Clin. Immunol., vol. 127, No. 6, 2011, pp. 1351-1355.
Datta & Sarvetnick, "Lymphocyte proliferation in immune-mediated diseases," Trends in Immunology, vol. 30, No. 9, 2009, pp. 430-438.
Del Peso, et al., "Rho proteins induce mestatic properties in vivo," Oncogene, vol. 15, 1997, pp. 3047-3057.
Deng, et al., "Design and synthesis of small molecule RhoA inhibitors: a new promising therapy for cardiovascular diseases?," J. Med. Chem., vol. 54, No. 13, 2011, pp. 4508-4522.
Desire, et al., "RAC1 inhibition targets amyloid precursor protein processing by gamma-secretase and decreases ABeta production in vitro and in vivo," vol. 280, No. 45, 2005, pp. 37516-37525.
Dixit, et al., "Ghrelin promotes thymopoiesis during aging," J. Clin. Invest., vol. 117, No. 10, 2007, pp. 2778-2790.
Dudakov, et al., "Interleukin-22 drives endogenous thymic regeneration in mice," Science, vol. 336, No. 6077, 2012, 11 pages.
Dunon & Imhof, "Mechanisms of Thymus Homing," Blood, vol. 81, No. 1, 1993, pp. 1-8.
Elbashir, et al., "Duplexes of 21-nucleotide RNAs mediate RNA interference in cultured mammalian cells," Nature, vol. 411, No. 6836, 2001, pp. 494-498.
Elbashir, et al., "RNA interference is mediated by 21- and 22-nucleotide RNAs," Genes Dev., vol. 15, 2001. pp. 188-200.
Eriksson, et al., "Small GTP-binding protein Rac is an essential mediator of vascular endothelial growth factor-induced endothelial fenestrations and vascular permeability," Circulation, vol. 107, No. 11, 2003, pp. 1532-1538.
Eysteinsdottir, et al., "The influence of partial or total thymectomy during open heart surgery in infants on the immune function later in life," Clin. Exp. Immunol, vol. 136, No. 2, 2004, pp. 349-355.
Fire, et al., "Potent and specific genetic interference by double-stranded RNA in Caenorhabditis elegans," Nature, vol. 391, 1998, pp. 806-811.
Florian, et al., "Cdc42 activity regulates hematopoietic stem cell aging and rejuvenation," Cell Stem Cell., vol. 10, No. 5, 2012, pp. 520-530.
Fritz & Kaina, "Rho GTPases: promising cellular targets for novel anticancer drugs," Current Cancer Drug Targets, vol. 6, No. 1, 2006, 14 pages.
Fritz, et al., "Rho GTPases are over-expressed in human tumors," Int. J. Cancer, vol. 81, No. 5, 1999, pp. 682-687.
Fryer & Field, "Rho, Rac, Pak and angiogenesis: old roles and newly identified responsibilities in endothelial cells," Cancer Letters, vol. 229, No. 1, 2005, pp. 13-23.
Gagnerault, et al., "Autoimmunity during thymectomy-induced lymphopenia: role of thymus ablation and initial effector T cell activation timing in nonobese diabetic mice," J. Imunnol., vol. 183, No. 8, 2009, pp. 4913-4920.
Gao, et al., "Rational design and characterization of a Rac GTPase-specific small molecule inihibitor," PNAS, vol. 101, No. 20, 2004, pp. 7618-7623.
Geenen, et al., "Quantification of T cell receptor rearrangement excision circles to estimate thymic function: an important new tool for endocrine-immune physiology," J. Endocrinol, vol. 176, 2003, pp. 305-311.
Goya, et al., "In vivo effects of growth hormone on thymus function in aging mice," Brain Behav. Immun., vol. 6, No. 4, 1992, pp. 341-354.
Giffith, et al., "Persistent degenerative changes in thymic organ function revealed by an inducible model of organ regrowth," Aging Cell., vol. 11, No. 1, 2012, pp. 169-177.
Haeusler, et al., "Purification and biochemical properties of Rac1, 2, 3 and the splice variant Rac1b," Methods in Enzymology, vol. 406, 2006, pp. 1-11.
Hall, "Rho GTPases and the actin cytoskeleton," Science, vol. 279, No. 5350, 1998, pp. 509-514.
Hall, et al., "Establishment and maintenance of a heterochromatin domain," Science, vol. 297, No. 5590, 2002, pp. 2232-2237.
Hammond, et al., "An RNA-directed nuclease mediates post-transcriptional gene silencing in *Drosophila* cells," Nature, vol. 404, No. 6775, 2000, pp. 293-296.
Heng, et al., "Getting back at nature: understanding thymic development and overcoming its atrophy," Curr. Opin. Pharmacol, vol. 10, No. 4, 2010, pp. 425-433.

(56) References Cited

OTHER PUBLICATIONS

Hong, et al., "Characterization of a Cdc42 protein inhibitor and its use as a molecular probe," J. Biol. Chem., vol. 288, No. 12, 2013, pp. 8531-8543.
Hutvagner, et al., "A cellular function for the RNA-interference enzyme Dicer in the maturation of the let-7 small temporal RNA," Science, vol. 293, No. 5531, 2001, pp. 834-838.
Ishikawa, et al., "Comparative antitumor activity of 5-fluorouracil and 5'-deoxy-5-fluorouridine in combination with radiation therapy in mice bearing colon 26 adenocarcinoma," Jpn. J. Cancer Res., vol. 80, No. 6, 1989, pp. 583-591.
Jakopin, "Nucleotide-binding oligomerization domain (NOD) inhibitors: a rational approach toward inhibition of NOD signaling pathway," J. Med. Chem. vol. 57, No. 16, 2014, pp. 6897-6918.
Jenuwein, "An RNA-guided pathway for the epigenome," Science, vol. 297, No. 5590, 2002, pp. 2215-2218.
Johnson, et al., "Subchronic oral toxicity and metabolite profiling of the p53 stabilizing agent, CP-31398, in rats and dogs," Toxicology, vol. 289, No. 2-3, 2011, pp. 141-150.
Jones & Jackson, "Ras-GRF Activates Ha-Ras, but Not N Ras or K-Ras 4B, Protein in Vivo," J. Biol. Chem., vol. 273, No. 3, 1998, pp. 1782-1787.
Kaminitz, et al., "Immunosuppressive therapy exacerbates autoimmunity in NOD mice and diminishes the protective activity of regulatory T cells," J. Autoimmun., vol. 35, No. 2, 2010, pp. 145-152.
Kapetanovic, et al., "Murine oncogenicity and pharmacokinetics studies of 9-cis-UAB30, an RXR agonist, for breast cancer chemoprevention," Int. J. Toxicol., vol. 29, No. 2, 2010, pp. 157-164.
Khosravi-Far, et al., "Increasing Complexity of Ras Signal Transduction: Involvement of Rho Family Proteins," Adv. Cancer Res., vol. 72, 1998, pp. 57-107.
King, et al., "Homeostatic expansion of T cells during immune insufficiency generates autoimmunity," Cell, vol. 117, 2004, pp. 265-277.
Knaus, et al., "Structural Requirements for PAK Activation by Rac GTPases," J. Biol. Chem., vol. 273, No. 34, pp. 21512-21518.
Lagos-Quintana, et al., "Identification of tissue-specific microRNAs from mouse," Curr. Biol., vol. 12, No. 9, 2002, pp. 735-739.
Invitation to Pay Fees Dated Mar. 27, 2019 for International Application No. PCT/US2019/013349, 2 Pages.
Search Report and Written Opinion Dated May 23, 2019 for International Application No. PCT/US19/13349, 15 pages.
Landgraf, et al., "A Mammalian microRNA Expression Atlas Based on Small RNA Library Sequencing," Cell, vol. 129, No. 7, 2007, pp. 1401-1414.
Lee, et al., "A four-week repeated study of intravenous toxicity of recombinant human interleukin-2 in Sprague-Dawley rats," Regul. Toxicol. Pharmacol., vol. 64, No. 2, 2012, pp. 253-262.
Lord-Fontaine, et al., "Local Inhibition of Rho Signaling by Cell-Permeable Recombinant Protein BA-210 Prevents Secondary Damage and Promotes Functional Recovery following Acute Spinal Cord Injury," J. Neurotrauma, vol. 25, No. 11, 2008, pp. 1309-1322.
Lynch, et al., "Thymic involution and immune reconstitution," Trends Immunol., vol. 30, No. 7, 2009, pp. 366-373.
Ma, et al., "Development of Second-Generation Small-Molecule RhoA Inhibitors with Enhanced Water Solubility, Tissue Potency, and Significant in vivo Efficacy," ChemMedChem., vol. 10, No. 1, 2015, pp. 193-206.
Manlulu, et al., "Video-assisted thoracic surgery thymectomy for nonthymomatous myasthenia gravis," Chest, vol. 128, No. 5, 2005, pp. 3454-3460.
Marinkovic, et al., "Inhibition of GTPase Rac1 in endothelium by 6-mercaptopurine results in immunosuppression in nonimmune cells: new target for an old drug," J. Immunol., vol. 192, No. 9, 2014, pp. 4370-4378.
Markert, et al., "Transplantation of thymus tissue in complete DiGeorge syndrome," N. Engl. J. Med., 1999, vol. 341, No. 16, 1999, pp. 1180-1189.
Markert, et al, "Postnatal thymus transplantation with immunosuppression as treatment for DiGeorge syndrome," Blood, vol. 104, No. 8, 2004, pp. 2574-281.
Markert, et al., "Review of 54 patients with complete DiGeorge anomaly enrolled in protocols for thymus transplantation: outcome of 44 consecutive transplants," Blood, vol. 109, No. 10, 2007, pp. 4539-4547.
Markert, et al., "Thymus transplantation," Clin. Immunol., vol. 135, No. 2, 2010, pp. 236-246.
Min, et al., "Sustained thymopoiesis and improvement in functional immunity induced by exogenous KGF administration in murine models of again," Blood, vol. 509, No. 6, 2007, pp. 2529-2537.
Molkentin & Dorn, "Cytoplasmic signaling pathways that regulate cardiac hypertrophy," Annu. Rev. Pyhsiol., vol. 63, 2001, pp. 391-426.
Montalvo-Ortiz, et al., "Characterization of EHop-016, novel small molecule inhibitor of Rac GTPase," J. Biol. Chem., vol. 287, No. 16, 2012, pp. 13228-13238.
Pogribny, et al., "Fractionated low-dose radiation exposure leads to accumulation of DNA damage and profound alterations in DNA and histone methylation in the murine thymus," Mol. Cancer. Res., vol. 3, No. 10, 2005, pp. 553-561.
Poy, et al., "A pancreatic islet-specific microRNA regulates insulin secretion," Nature, vol. 432, No. 7014, 2004, pp. 226-230.
Rebillard, et al., "Acid sphingomyelinase deficiency protects from cisplatin-inducedgastrointestinal damage," Oncogene, vol. 27, No. 51, 2008, pp. 6590-6595.
Rickard, et al., "Identification of benzimidazole diamides as selective inhibitors of the nucleotide-binding oligomerization domain 2 (NOD2) signaling pathway," PloS One, vol. 8, No. 8, 2013, pp. 69619.
Ridley, "The GTP-binding protein Rho," Int. J. Biochem. Cell. Biol., vol. 29, No. 11, 1997, pp. 1225-1229.
Sahai, et al., "RHO-GTPases and cancer," Nat. Rev. Cancer, vol. 2, 2002, pp. 133-142.
Schuurman, et al., "Chemicals trophic for the thymus: risk for immunodeficiency and autoimmunity," Int. J. Immunopharmacol., vol. 14, No. 3, 1992, pp. 369-375.
Seandel, et al., "Generation of a functional durable vascular niche by the adenoviral E40RF1 gene," PNAS, vol. 105, No. 49, 2008, pp. 19288-19293.
Seok, et al., "Isoflavone Attenuates Vascular Contraction through Inhibition of the RhoA/Rho-Kinase Signaling Pathway," J. Pharmacol. Exp. Ther., vol. 326, No. 3, 2008, pp. 991-998.
Shang, et al., "Rational design of small molecule inhibitors targeting RhoA subfamily Rho GTPases," Chem Biol., vol. 19, No. 6, 2012, pp. 699-710.
Soga, et al., "Rho family GTPases regulate VEGF-stimulated endothelial cell motility," Exp. Cell Res., vol. 269, No. 1, 2001, pp. 73-87.
Su, et al., "Evaluation of the efficacy, toxicity and safety of vinorelbine incorporated in a lipid emulsion," Int. J. Pharm., vol. 411, No. 1-2, 2011, pp. 188-196.
Surviladze, et al., "Identification of a Small GTPase Inhibitor using a High-Throughput Flow Cytometry Bead-Based Multiplex Assay," J. Biomol., vol. 15, No. 1, 2010, pp. 10-20.
Tulinska, et al., "Immunotoxicity of ethyl-4-isothiocyanatobutanoate in male Wistar rats," vol. 145, No. 2-3, 2000, pp. 217-225.
Volpe, et al., "Regulation of heterochromatic silencing and histone H3 lysine-9 methylation by RNAi," Science, vol. 297, No. 5588, 2002, pp. 1833-1837.
Wianny & Zernicka-Goetz "Specific interference with gene function by double-stranded RNA in early mouse development," Nat. Cell. Biol., vol. 2, No. 2, 2000, pp. 70-75.
Zlotoff & Bhandoola, "Hematopoietic progenitor migration to the adult thymus," Annals of the New York Academy of Sciences, vol. 1217, 2011, pp. 122-138.
Zou, et al., "Defective positive selection results in T cell lymphopenia and increased autoimmune diabetes in ADAP-deficient BDC2.5-C57BL/6 mice," Eur. J. Immunol., vol. 38, No. 4, 2008, pp. 986-994.

(56) References Cited

OTHER PUBLICATIONS

Zusman, et al., "T cell kinetics and apoptosis in immune organs and mammary tumors of rats treated with cyclophosphamide and soluble tumor-associated antigens," In Vivo, vol. 16, No. 6, 2002, pp. 567-576.
Zvelebil, et al., "Flavopiridol Hoechst AG," IDrugs., vol. 1, No. 2, 1998, pp. 241-246.

* cited by examiner

FIG. 13

NOD2

MGEEGGSASHDEEERASVLLGHSPGCEMCSQEAFQAQRSQLVELLVSGSLEGFESVLDWLLS
WEVLSWEDYEGFHLLGQPLSHLARRLLDTVWNKGTWACQKLIAAAQEAQADSQSPKLHGCW
DPHSLHPARDLQSHRPAIVRRLHSHVENMLDLAWERGFVSQYECDEIRLPIFTPSQRARRLLDL
ATVKANGLAAFLLQHVQELPVPLALPLEAATCKKYMAKLRTTVSAQSRFLSTYDGAETLCLEDIY
TENVLEVWADVGMAGPPQKSPATLGLEELFSTPGHLNDDADTVLVVGEAGSGKSTLLQRLHLL
WAAGQDFQEFLFVFPFSCRQLQCMAKPLSVRTLLFEHCCWPDVGQEDIFQLLLDHPDRVLLTF
DGFDEFKFRFTDRERHCSPTDPTSVQTLLFNLLQGNLLKNARKVVTSRPAAVSAFLRKYIRTEF
NLKGFSEQGIELYLRKRHHEPGVADRLIRLLQETSALHGLCHLPVFSWMVSKCHQELLLQEGG
SPKTTTDMYLLILQHFLLHATPPDSASQGLGPSLLRGRLPTLLHLGRLALWGLGMCCYVFSAQQ
LQAAQVSPDDISLGFLVRAKGVVPGSTAPLEFLHITFQCFFAAFYLALSADVPPALLRHLFNCGR
PGNSPMARLLPTMCIQASEGKDSSVAALLQKAEPHNLQITAAFLAGLLSREHWGLLAECQTSE
KALLRRQACARWCLARSLRKHFHSIPPAAPGEAKSVHAMPGFIWLIRSLYEMQEERLARKAAR
GLNVGHLKLTFCSVGPTECAALAFVLQHLRRPVALQLDYNSVGDIGVEQLLPCLGVCKALYLRD
NNISDRGICKLIECALHCEQLQKLALFNNKLTDGCAHSMAKLLACRQNFLALRLGNNYITAAGAQ
VLAEGLRGNTSLQFLGFWGNRVGDEGAQALAEALGDHQSLRWLSLVGNNIGSVGAQALALML
AKNVMLEELCLEENHLQDEGVCSLAEGLKKNSSLKILKLSNNCITYLGAEALLQALERNDTILEV
WLRGNTFSLEEVDKLGCRDTRLLL (SEQ ID NO: 1)

RhoA

MAAIRKKLVIVGDGACGKTCLLIVFSKDQFPEVYVPTVFENYVADIEVDGKQVELALWD
TAGQEDYDRLRPLSYPDTDVILMCFSIDSPDSLENIPEKWTPEVKHFCPNVPIILVGNKK
DLRNDEHTRRELAKMKQEPVKPEEGRDMANRIGAFGYMECSAKTKDGVREVFEMAT
RAALQARRGKKKSGCLVL (SEQ ID NO: 2)

Rac1

MQAIKCVVVGDGAVGKTCLLISYTTNAFPGEYIPTVFDNYSANVMVDGKPVNLGLWDT
AGQEDYDRLRPLSYPQTDVFLICFSLVSPASFENVRAKWYPEVRHHCPNTPIILVGTKL
DLRDDKDTIEKLKEKKLTPITYPQGLAMAKEIGAVKYLECSALTQRGLKTVFDEAIRAVL
CPPPVKKRKRKCL (SEQ ID NO: 3)

IL-22

MAALQKSVSSFLMGTLATSCLLLLALLVQGGAAAPISSHCRLDKSNFQQPYITNRTFML
AKEASLADNNTDVRLIGEKLFHGVSMSERCYLMKQVLNFTLEEVLFPQSDRFQPYMQE
VVPFLARLSNRLSTCHIEGDDLHIQRNVQKLKDTVKKLGESGEIKAIGELDLLFMSLRNA
CI (SEQ ID NO: 4)

FIG. 13 (cont'd)

IL-23 p19 subunit

MLGSRAVMLLLLLPWTAQGRAVPGGSSPAWTQCQQLSQKLCTLAWSAHPLVGHMDL
REEGDEETTNDVPHIQCGDGCDPQGLRDNSQFCLQRIHQGLIFYEKLLGSDIFTGEPS
LLPDSPVGQLHASLLGLSQLLQPEGHHWETQQIPSLSPSQPWQRLLLRFKILRSLQAF
VAVAARVFAHGAATLSP (SEQ ID NO: 5)

IL-23 p40 subunit

MCHQQLVISWFSLVFLASPLVAIWELKKDVYVVELDWYPDAPGEMVVLTCDTPEEDGI
TWTLDQSSEVLGSGKTLTIQVKEFGDAGQYTCHKGGEVLSHSLLLLHKKEDGIWSTDIL
KDQKEPKNKTFLRCEAKNYSGRFTCWWLTTISTDLTFSVKSSRGSSDPQGVTCGAAT
LSAERVRGDNKEYEYSVECQEDSACPAAEESLPIEVMVDAVHKLKYENYTSSFFIRDII
KPDPPKNLQLKPLKNSRQVEVSWEYPDTWSTPHSYFSLTFCVQVQGKSKREKKDRVF
TDKTSATVICRKNASISVRAQDRYYSSSWSEWASVPCS (SEQ ID NO: 6)

BMP4

MLMVVLLCQVLLGGASHASLIPETGKKKVAEIQGHAGGRRSGQSHELLRDFEATLLQM
FGLRRRPQPSKSAVIPDYMRDLYRLQSGEEEEEQIHSTGLEYPERPASRANTVRSFHH
EEHLENIPGTSENSAFRFLFNLSSIPENEVISSAELRLFREQVDQGPDWERGFHRINIYE
VMKPPAEVVPGHLITRLLDTRLVHHNVTRWETFDVSPAVLRWTREKQPNYGLAIEVTH
LHQTRTHQGQHVRISRSLPQGSGNWAQLRPLLVTFGHDGRGHALTRRRRAKRSPKH
HSQRARKKNKNCRRHSLYVDFSDVGWNDWIVAPPGYQAFYCHGDCPFPLADHLNST
NHAIVQTLVNSVNSSIPKACCVPTELSAISMLYLDEYDKVVLKNYQEMVVEGCGCR
(SEQ ID NO: 7)

SEQUENCE LISTING

```
<160> NUMBER OF SEQ ID NOS: 12

<210> SEQ ID NO 1
<211> LENGTH: 1040
<212> TYPE: PRT
<213> ORGANISM: Homo sapiens

<400> SEQUENCE: 1

Met Gly Glu Glu Gly Gly Ser Ala Ser His Asp Glu Glu Glu Arg Ala
1               5                   10                  15

Ser Val Leu Leu Gly His Ser Pro Gly Cys Glu Met Cys Ser Gln Glu
            20                  25                  30

Ala Phe Gln Ala Gln Arg Ser Gln Leu Val Glu Leu Leu Val Ser Gly
        35                  40                  45

Ser Leu Glu Gly Phe Glu Ser Val Leu Asp Trp Leu Leu Ser Trp Glu
    50                  55                  60

Val Leu Ser Trp Glu Asp Tyr Glu Gly Phe His Leu Leu Gly Gln Pro
65                  70                  75                  80

Leu Ser His Leu Ala Arg Arg Leu Leu Asp Thr Val Trp Asn Lys Gly
                85                  90                  95

Thr Trp Ala Cys Gln Lys Leu Ile Ala Ala Ala Gln Glu Ala Gln Ala
            100                 105                 110

Asp Ser Gln Ser Pro Lys Leu His Gly Cys Trp Asp Pro His Ser Leu
        115                 120                 125

His Pro Ala Arg Asp Leu Gln Ser His Arg Pro Ala Ile Val Arg Arg
    130                 135                 140

Leu His Ser His Val Glu Asn Met Leu Asp Leu Ala Trp Glu Arg Gly
145                 150                 155                 160
```

-continued

```
Phe Val Ser Gln Tyr Glu Cys Asp Glu Ile Arg Leu Pro Ile Phe Thr
                165                 170                 175

Pro Ser Gln Arg Ala Arg Arg Leu Leu Asp Leu Ala Thr Val Lys Ala
            180                 185                 190

Asn Gly Leu Ala Ala Phe Leu Leu Gln His Val Gln Glu Leu Pro Val
        195                 200                 205

Pro Leu Ala Leu Pro Leu Glu Ala Ala Thr Cys Lys Lys Tyr Met Ala
    210                 215                 220

Lys Leu Arg Thr Thr Val Ser Ala Gln Ser Arg Phe Leu Ser Thr Tyr
225                 230                 235                 240

Asp Gly Ala Glu Thr Leu Cys Leu Glu Asp Ile Tyr Thr Glu Asn Val
                245                 250                 255

Leu Glu Val Trp Ala Asp Val Gly Met Ala Gly Pro Pro Gln Lys Ser
            260                 265                 270

Pro Ala Thr Leu Gly Leu Glu Glu Leu Phe Ser Thr Pro Gly His Leu
        275                 280                 285

Asn Asp Asp Ala Asp Thr Val Leu Val Val Gly Glu Ala Gly Ser Gly
    290                 295                 300

Lys Ser Thr Leu Leu Gln Arg Leu His Leu Leu Trp Ala Ala Gly Gln
305                 310                 315                 320

Asp Phe Gln Glu Phe Leu Phe Val Phe Pro Phe Ser Cys Arg Gln Leu
                325                 330                 335

Gln Cys Met Ala Lys Pro Leu Ser Val Arg Thr Leu Leu Phe Glu His
            340                 345                 350

Cys Cys Trp Pro Asp Val Gly Gln Glu Asp Ile Phe Gln Leu Leu Leu
        355                 360                 365

Asp His Pro Asp Arg Val Leu Leu Thr Phe Asp Gly Phe Asp Glu Phe
    370                 375                 380

Lys Phe Arg Phe Thr Asp Arg Glu Arg His Cys Ser Pro Thr Asp Pro
385                 390                 395                 400

Thr Ser Val Gln Thr Leu Leu Phe Asn Leu Leu Gln Gly Asn Leu Leu
                405                 410                 415

Lys Asn Ala Arg Lys Val Val Thr Ser Arg Pro Ala Ala Val Ser Ala
            420                 425                 430

Phe Leu Arg Lys Tyr Ile Arg Thr Glu Phe Asn Leu Lys Gly Phe Ser
        435                 440                 445

Glu Gln Gly Ile Glu Leu Tyr Leu Arg Lys Arg His His Glu Pro Gly
    450                 455                 460

Val Ala Asp Arg Leu Ile Arg Leu Leu Gln Glu Thr Ser Ala Leu His
465                 470                 475                 480

Gly Leu Cys His Leu Pro Val Phe Ser Trp Met Val Ser Lys Cys His
                485                 490                 495

Gln Glu Leu Leu Leu Gln Glu Gly Gly Ser Pro Lys Thr Thr Thr Asp
            500                 505                 510

Met Tyr Leu Leu Ile Leu Gln His Phe Leu Leu His Ala Thr Pro Pro
        515                 520                 525

Asp Ser Ala Ser Gln Gly Leu Gly Pro Ser Leu Leu Arg Gly Arg Leu
    530                 535                 540

Pro Thr Leu Leu His Leu Gly Arg Leu Ala Leu Trp Gly Leu Gly Met
545                 550                 555                 560

Cys Cys Tyr Val Phe Ser Ala Gln Gln Leu Gln Ala Ala Gln Val Ser
                565                 570                 575
```

-continued

```
Pro Asp Asp Ile Ser Leu Gly Phe Leu Val Arg Ala Lys Gly Val Val
            580                 585                 590

Pro Gly Ser Thr Ala Pro Leu Glu Phe Leu His Ile Thr Phe Gln Cys
        595                 600                 605

Phe Phe Ala Ala Phe Tyr Leu Ala Leu Ser Ala Asp Val Pro Pro Ala
    610                 615                 620

Leu Leu Arg His Leu Phe Asn Cys Gly Arg Pro Gly Asn Ser Pro Met
625                 630                 635                 640

Ala Arg Leu Leu Pro Thr Met Cys Ile Gln Ala Ser Glu Gly Lys Asp
                645                 650                 655

Ser Ser Val Ala Ala Leu Leu Gln Lys Ala Glu Pro His Asn Leu Gln
            660                 665                 670

Ile Thr Ala Ala Phe Leu Ala Gly Leu Leu Ser Arg Glu His Trp Gly
        675                 680                 685

Leu Leu Ala Glu Cys Gln Thr Ser Glu Lys Ala Leu Leu Arg Arg Gln
    690                 695                 700

Ala Cys Ala Arg Trp Cys Leu Ala Arg Ser Leu Arg Lys His Phe His
705                 710                 715                 720

Ser Ile Pro Pro Ala Ala Pro Gly Glu Ala Lys Ser Val His Ala Met
                725                 730                 735

Pro Gly Phe Ile Trp Leu Ile Arg Ser Leu Tyr Glu Met Gln Glu Glu
            740                 745                 750

Arg Leu Ala Arg Lys Ala Ala Arg Gly Leu Asn Val Gly His Leu Lys
        755                 760                 765

Leu Thr Phe Cys Ser Val Gly Pro Thr Glu Cys Ala Ala Leu Ala Phe
    770                 775                 780

Val Leu Gln His Leu Arg Arg Pro Val Ala Leu Gln Leu Asp Tyr Asn
785                 790                 795                 800

Ser Val Gly Asp Ile Gly Val Glu Gln Leu Leu Pro Cys Leu Gly Val
                805                 810                 815

Cys Lys Ala Leu Tyr Leu Arg Asp Asn Asn Ile Ser Asp Arg Gly Ile
            820                 825                 830

Cys Lys Leu Ile Glu Cys Ala Leu His Cys Glu Gln Leu Gln Lys Leu
        835                 840                 845

Ala Leu Phe Asn Asn Lys Leu Thr Asp Gly Cys Ala His Ser Met Ala
    850                 855                 860

Lys Leu Leu Ala Cys Arg Gln Asn Phe Leu Ala Leu Arg Leu Gly Asn
865                 870                 875                 880

Asn Tyr Ile Thr Ala Ala Gly Ala Gln Val Leu Ala Glu Gly Leu Arg
                885                 890                 895

Gly Asn Thr Ser Leu Gln Phe Leu Gly Phe Trp Gly Asn Arg Val Gly
            900                 905                 910

Asp Glu Gly Ala Gln Ala Leu Ala Glu Ala Leu Gly Asp His Gln Ser
        915                 920                 925

Leu Arg Trp Leu Ser Leu Val Gly Asn Asn Ile Gly Ser Val Gly Ala
    930                 935                 940

Gln Ala Leu Ala Leu Met Leu Ala Lys Asn Val Met Leu Glu Glu Leu
945                 950                 955                 960

Cys Leu Glu Glu Asn His Leu Gln Asp Glu Gly Val Cys Ser Leu Ala
                965                 970                 975

Glu Gly Leu Lys Lys Asn Ser Ser Leu Lys Ile Leu Lys Leu Ser Asn
            980                 985                 990

Asn Cys Ile Thr Tyr Leu Gly Ala  Glu Ala Leu Leu Gln  Ala Leu Glu
```

```
        995                 1000                1005

Arg Asn  Asp Thr Ile Leu Glu  Val Trp Leu Arg Gly  Asn Thr Phe
    1010                 1015                1020

Ser Leu  Glu Glu Val Asp Lys  Leu Gly Cys Arg Asp  Thr Arg Leu
    1025                 1030                1035

Leu Leu
    1040


<210> SEQ ID NO 2
<211> LENGTH: 193
<212> TYPE: PRT
<213> ORGANISM: Homo sapiens

<400> SEQUENCE: 2

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
            180                 185                 190

Leu


<210> SEQ ID NO 3
<211> LENGTH: 190
<212> TYPE: PRT
<213> ORGANISM: Homo sapiens

<400> SEQUENCE: 3

Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Gly
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80
```

```
Cys Phe Ser Leu Val Ser Pro Ala Ser Phe Glu Asn Val Arg Ala Lys
                85                  90                  95

Trp Tyr Pro Glu Val Arg His His Cys Pro Asn Thr Pro Ile Ile Leu
            100                 105                 110

Val Gly Thr Lys Leu Asp Leu Arg Asp Asp Lys Asp Thr Ile Glu Lys
        115                 120                 125

Leu Lys Glu Lys Lys Leu Thr Pro Ile Thr Tyr Pro Gln Gly Leu Ala
    130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu
            180                 185                 190


<210> SEQ ID NO 4
<211> LENGTH: 179
<212> TYPE: PRT
<213> ORGANISM: Homo sapiens

<400> SEQUENCE: 4

Met Ala Ala Leu Gln Lys Ser Val Ser Ser Phe Leu Met Gly Thr Leu
1               5                   10                  15

Ala Thr Ser Cys Leu Leu Leu Leu Ala Leu Leu Val Gln Gly Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
        115                 120                 125

Leu Ser Thr Cys His Ile Glu Gly Asp Asp Leu His Ile Gln Arg Asn
    130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile


<210> SEQ ID NO 5
<211> LENGTH: 189
<212> TYPE: PRT
<213> ORGANISM: Homo sapiens

<400> SEQUENCE: 5

Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
            20                  25                  30
```

-continued

```
Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185


<210> SEQ ID NO 6
<211> LENGTH: 328
<212> TYPE: PRT
<213> ORGANISM: Homo sapiens

<400> SEQUENCE: 6

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220
```

```
Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325


<210> SEQ ID NO 7
<211> LENGTH: 402
<212> TYPE: PRT
<213> ORGANISM: Homo sapiens

<400> SEQUENCE: 7

Met Leu Met Val Val Leu Leu Cys Gln Val Leu Leu Gly Gly Ala Ser
1               5                   10                  15

His Ala Ser Leu Ile Pro Glu Thr Gly Lys Lys Lys Val Ala Glu Ile
            20                  25                  30

Gln Gly His Ala Gly Gly Arg Arg Ser Gly Gln Ser His Glu Leu Leu
        35                  40                  45

Arg Asp Phe Glu Ala Thr Leu Leu Gln Met Phe Gly Leu Arg Arg Arg
    50                  55                  60

Pro Gln Pro Ser Lys Ser Ala Val Ile Pro Asp Tyr Met Arg Asp Leu
65                  70                  75                  80

Tyr Arg Leu Gln Ser Gly Glu Glu Glu Glu Glu Gln Ile His Ser Thr
                85                  90                  95

Gly Leu Glu Tyr Pro Glu Arg Pro Ala Ser Arg Ala Asn Thr Val Arg
            100                 105                 110

Ser Phe His His Glu Glu His Leu Glu Asn Ile Pro Gly Thr Ser Glu
        115                 120                 125

Asn Ser Ala Phe Arg Phe Leu Phe Asn Leu Ser Ser Ile Pro Glu Asn
    130                 135                 140

Glu Val Ile Ser Ser Ala Glu Leu Arg Leu Phe Arg Glu Gln Val Asp
145                 150                 155                 160

Gln Gly Pro Asp Trp Glu Arg Gly Phe His Arg Ile Asn Ile Tyr Glu
                165                 170                 175

Val Met Lys Pro Pro Ala Glu Val Val Pro Gly His Leu Ile Thr Arg
            180                 185                 190

Leu Leu Asp Thr Arg Leu Val His His Asn Val Thr Arg Trp Glu Thr
        195                 200                 205

Phe Asp Val Ser Pro Ala Val Leu Arg Trp Thr Arg Glu Lys Gln Pro
    210                 215                 220

Asn Tyr Gly Leu Ala Ile Glu Val Thr His Leu His Gln Thr Arg Thr
225                 230                 235                 240

His Gln Gly Gln His Val Arg Ile Ser Arg Ser Leu Pro Gln Gly Ser
                245                 250                 255

Gly Asn Trp Ala Gln Leu Arg Pro Leu Leu Val Thr Phe Gly His Asp
```

```
            260                 265                 270

Gly Arg Gly His Ala Leu Thr Arg Arg Arg Arg Ala Lys Arg Ser Pro
        275                 280                 285

Lys His His Ser Gln Arg Ala Arg Lys Lys Asn Lys Asn Cys Arg Arg
    290                 295                 300

His Ser Leu Tyr Val Asp Phe Ser Asp Val Gly Trp Asn Asp Trp Ile
305                 310                 315                 320

Val Ala Pro Pro Gly Tyr Gln Ala Phe Tyr Cys His Gly Asp Cys Pro
                325                 330                 335

Phe Pro Leu Ala Asp His Leu Asn Ser Thr Asn His Ala Ile Val Gln
            340                 345                 350

Thr Leu Val Asn Ser Val Asn Ser Ser Ile Pro Lys Ala Cys Cys Val
        355                 360                 365

Pro Thr Glu Leu Ser Ala Ile Ser Met Leu Tyr Leu Asp Glu Tyr Asp
    370                 375                 380

Lys Val Val Leu Lys Asn Tyr Gln Glu Met Val Val Glu Gly Cys Gly
385                 390                 395                 400

Cys Arg


<210> SEQ ID NO 8
<211> LENGTH: 16
<212> TYPE: PRT
<213> ORGANISM: Artificial Sequence
<220> FEATURE:
<223> OTHER INFORMATION: Rac1 Inhibitor W56

<400> SEQUENCE: 8

Met Val Asp Gly Lys Pro Val Asn Leu Gly Leu Trp Asp Thr Ala Gly
1               5                   10                  15


<210> SEQ ID NO 9
<211> LENGTH: 22
<212> TYPE: RNA
<213> ORGANISM: Mus musculus

<400> SEQUENCE: 9

uagcaccauu ugaaaucggu ua                                              22


<210> SEQ ID NO 10
<211> LENGTH: 22
<212> TYPE: RNA
<213> ORGANISM: Mus musculus

<400> SEQUENCE: 10

ugaccgauuu cuccuggugu uc                                              22


<210> SEQ ID NO 11
<211> LENGTH: 20
<212> TYPE: RNA
<213> ORGANISM: Homo sapiens

<400> SEQUENCE: 11

uagcaccauu ugaaaucggu                                                 20


<210> SEQ ID NO 12
<211> LENGTH: 88
<212> TYPE: RNA
```

-continued

```
<213> ORGANISM: Mus musculus

<400> SEQUENCE: 12

aucucuuaca caggcugacc gauuucuccu gguguucaga gucuguuuuu gucuagcacc      60

auuugaaauc gguuaugaug uaggggga                                         88
```

COMPOSITIONS AND METHODS TO PROMOTE THYMIC REGENERATION

CROSS-REFERENCE TO RELATED APPLICATIONS

This application is a US National Phase Application based on PCT/US2019/013349, filed Jan. 11, 2019, which claims priority to U.S. Provisional Patent Application No. 62/616,252 filed Jan. 11, 2018, the entire contents of both of which are incorporated by reference herein.

STATEMENT REGARDING FEDERALLY SPONSORED RESEARCH OR DEVELOPMENT

This invention was made with government support under CA176376 awarded by the National Institutes of Health. The government has certain rights in the invention.

STATEMENT REGARDING SEQUENCE LISTING

The Sequence Listing associated with this application is provided in text format in lieu of a paper copy and is hereby incorporated by reference into the specification. The name of the text file containing the Sequence Listing is 2BG5585 ST25.txt. The text file is 22.6 KB, was created on Jul. 6, 2020, and is being submitted electronically via EFS-Web.

FIELD OF THE DISCLOSURE

The disclosure provides compositions and methods to promote thymic regeneration. The compositions and methods can inhibit nucleotide-binding oligomerization domain-containing protein 2 (NOD2), Rho GTPases, and/or microRNA 29c (miR29c). The inhibition of NOD2, Rho GTPases, and/or miR29c can upregulate regenerative molecules, such as interleukin (IL)-22, IL-23, and bone morphogenetic protein 4 (BMP4).

BACKGROUND OF THE DISCLOSURE

The thymus is the primary site of T cell development and is extremely sensitive to damage, while concurrently possessing a remarkable regenerative capacity. Previous studies have revealed two crucial pathways that promote thymic regeneration; namely the production of interleukin (IL)-22 by innate lymphoid cells (ILCs) and bone morphogenetic protein 4 (BMP4) by endothelial cells (ECs).

SUMMARY OF THE DISCLOSURE

The current disclosure provides compositions and methods that promote thymic regeneration. In particular embodiments, the compositions and methods promote thymic regeneration by reducing or inhibiting nucleotide-binding oligomerization domain-containing protein 2 (NOD2), Rho GTPases, and/or microRNA 29c (miR29c). Inhibition of NOD2, Rho GTPases, and/or miR29c can upregulate regenerative molecules, such as interleukin (IL)-22, IL-23, and bone morphogenetic protein 4 (BMP4). Thymic regeneration is useful in subjects with thymic damage due to, for example, age, infection or cancer therapies.

The number of DP thymocytes are significantly reduced after TBI, for example by 90% at day 4. In contrast, the ECs were less sensitive to TBI and did not have a reduction in cell number after treatment, suggesting a level of radio-resistance.

FIGS. 2A-2D. EC-derived bone morphogenetic protein 4 (BMP4) is crucial for thymic regeneration. Thymuses were pooled from 6-week-old C57BL/6 mice and microarray analysis was performed on CD45− cells enriched from either untreated mice (d0) or 4, and 7 days after TBI (550 cGy, n=3/timepoint with each n pooled from 3-5 mice). Volcano plot outlining genes that changed >1.5 fold, $p<0.05$ and fold change of selected Rho genes at day 4 and day 7. Statistics represent a comparison to day 0. See Sci. Immunol. 2018 Jan. 12:3(19).

(2A) Bmp4 expression was upregulated in ECs sorted from the thymus at day 4 after TBI compared with day 0. (2B) Specific deletion of ECs revealed a significantly lower thymic cellularity than when ECs are not deleted, (2C) suggesting a crucial role for ECs in thymic regeneration. (2D) Additionally, pharmacological inhibition of the BMP type I receptor resulted in a significantly lower thymic cellularity, compared with control vehicle treated mice.

Figure 1:
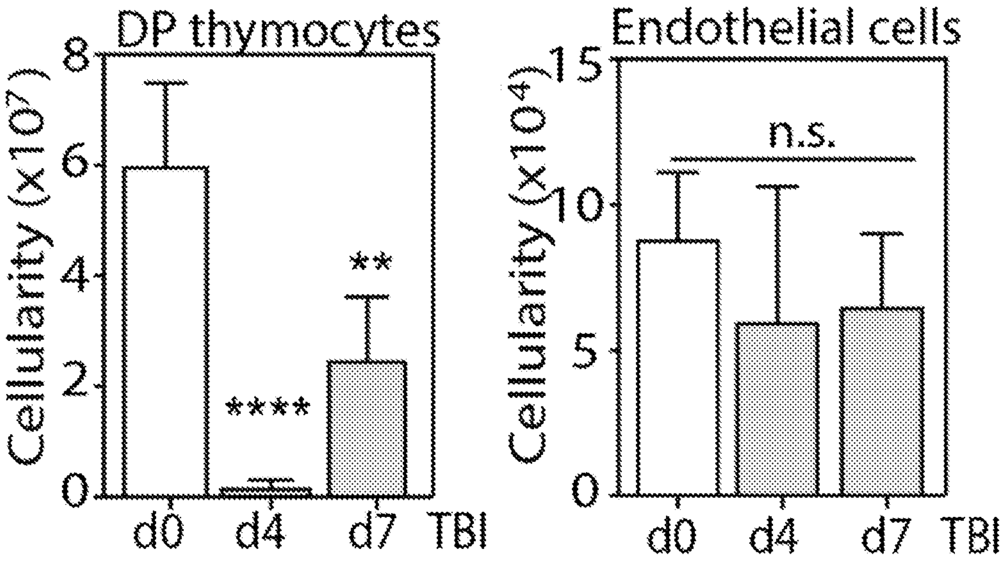
FIG. 1. Endothelial cells (ECs) are more resistant to irradiation than double positive (DP; (CD4+CD8+) thymocytes. The thymi from 6 week old C57BL/6 mice were harvested (n=4-5 mice per treatment group) at day 0 (untreated), day 4 or day 7 after total body irradiation (TBI, 550 cGy). The thymi were collected in phosphate buffered saline (PBS) plus 5% bovine serum albumin (BSA) and mechanically dissociated using a scissors, followed by enzymatic digestion in Dulbecco's Modified Eagle Medium (DMEM) plus 0.2 mg/ml DNase and 1 mg/ml collagenase) for 1 hour at 37° C. shaking at 600 rpm on a thermoblock with intermittent pipetting to ensure digestion. The cells were counted and prepared for extracellular staining to mark the distinct populations. The samples were analyzed by flow cytometry and subsequent cell population numbers were calculated. DP thymocytes were gated on CD45+CD4+CD8+ populations, and ECs were CD45-MHCII-EpCAM-PDGR1α-CD31+ populations.
Figure 2A:
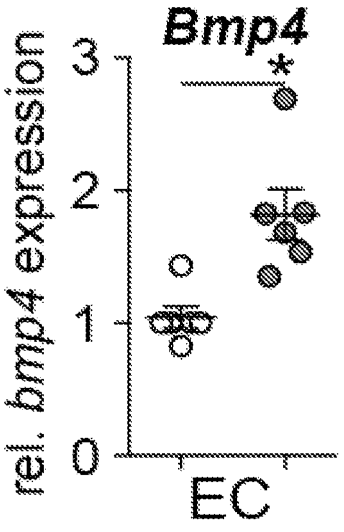
Figure 2B:
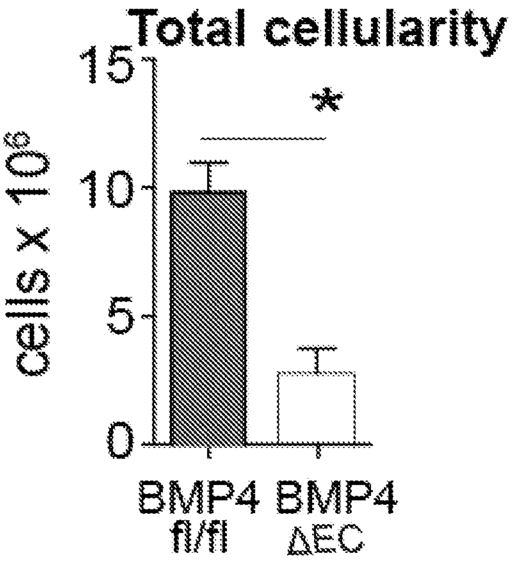
Figure 2C:
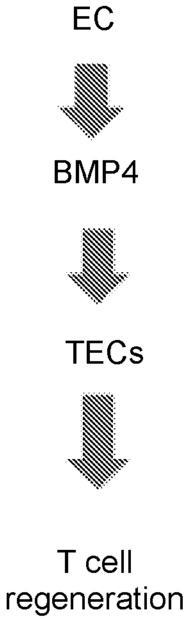
Figure 2D:
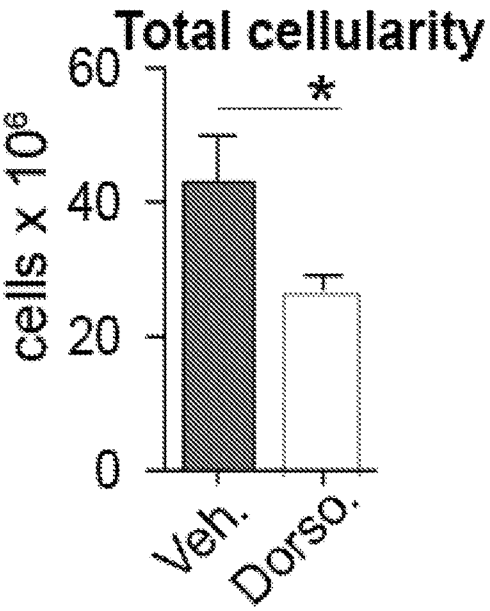
Figure 3:
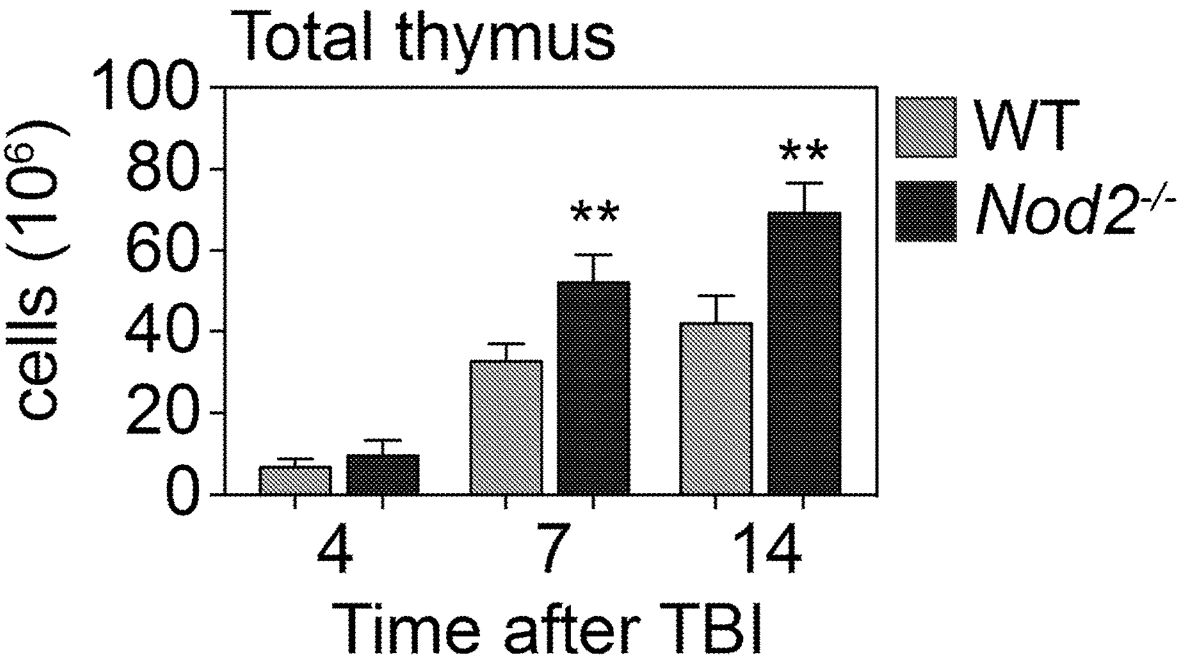

FIG. 3. Abrogation of NOD2 enhances thymic regeneration after acute injury (shown here as TBI). The thymi from 6 week old C57BL/6 mice and 6 week old Nod2−/− mice (B6.129S1-Nod2tm1Flv/J, www.jax.org/strain/005763) were harvested (n=5 mice per treatment group) at day 4, day 7 or day 14 after TBI. The thymi were digested as described above in relation to FIG. 1, and total cellularity was calculated.

Nod2-deficient thymi have a higher cellularity than wild-type (WT) counterparts after TBI, suggesting a more rapid and enhanced thymic recovery after injury when Nod2 is absent.

Figure 4:
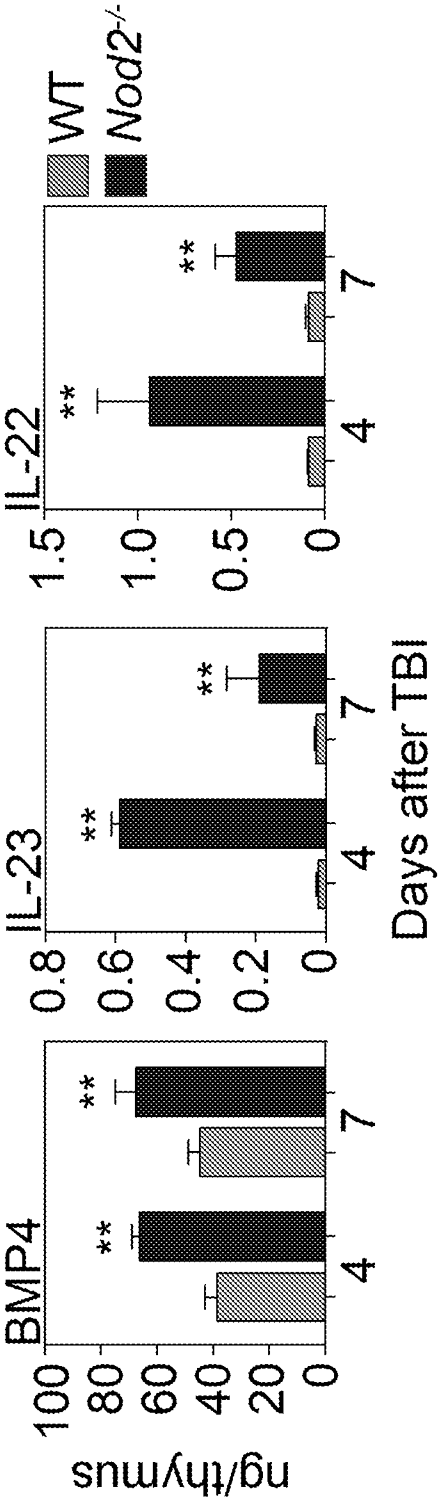

FIG. 4. NOD2 suppresses the production of the regeneration-associated factors (RAFs) BMP4, IL-23 and IL-22, the three of which have been shown to drive thymic regeneration. The thymus from 6 week old C57BL/6 mice and 6 week old $Nod2^{-/-}$ mice were harvested at day 4 and day 7 after TBI, and lysed in radioimmunoprecipitation assay (RIPA) buffer (50 mM Tris pH7.8, 150 mM NaCl, 0.5 Mm EDTA, 1.33% NP40, 0.13% SDS, 0.066% deoxycholate, plus protease inhibitors), using a tissue homogenizer and aliquoted at 10 mg/ml. Enzyme-linked immunosorbent assays (ELISAs) were performed to determine levels of BMP4 (LS Bio, LS-F13543), IL-23 (Biolegend, 433704), and IL-22 (Invitrogen, BMS6022). To obtain absolute protein quantification the samples were normalized to thymus weight.

Nod2-deficient thymi have significantly higher levels of BMP4, IL-23 and IL-22 compared with WT mice after TBI, suggesting NOD2 plays a role in suppressing the production of these RAFs.

Figure 5:
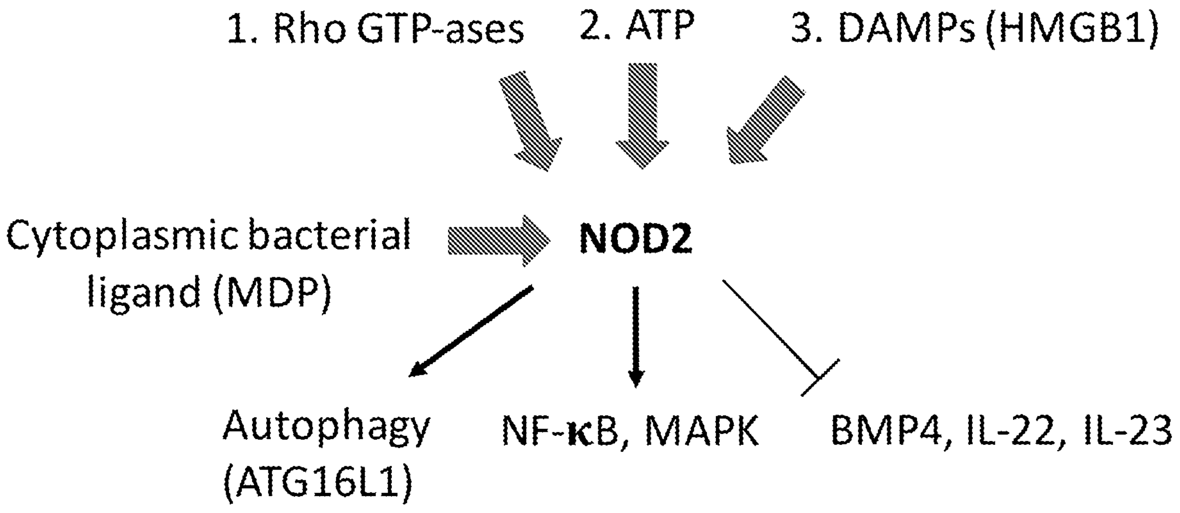

FIG. 5. Schematic showing proposed mechanisms that modulate NOD2 signaling. This FIG. represents the multiple factors that have been implicated to modulate NOD2 signaling, which in turn can inhibit the production of BMP4, IL-23 and IL-22, including Rho GTPases, ATP and mitochondrial stress, and several other damage-associated molecular patterns (DAMPs) including high-mobility group box 1 (HMGB1).

Figure 6:
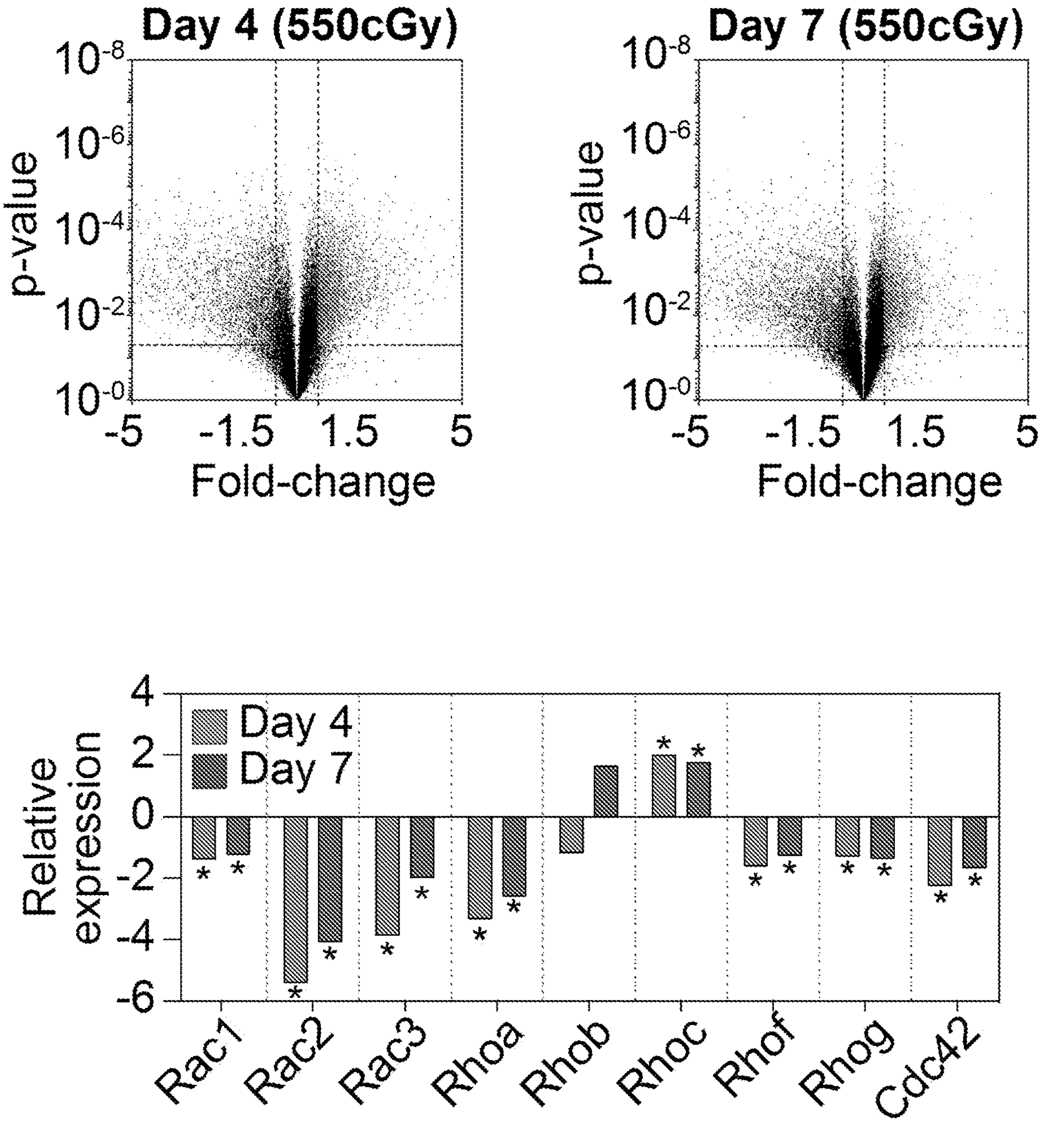

FIG. 6. Rho GTPases are downregulated in the thymus at days 4 and 7 after TBI. Transcriptomic analysis was carried out from CD45 negative populations of the WT thymus. Several Rho GTPase family member are reduced in the CD45 negative fraction of the thymus (which includes the ECs) after TBI at days 4 and 7 compared with their expression levels at day 0. The reduced expression is observed in Rac1, Rac2, Rac3, RhoA, RhoF, RhoG and Cdc42.

Figure 7A:
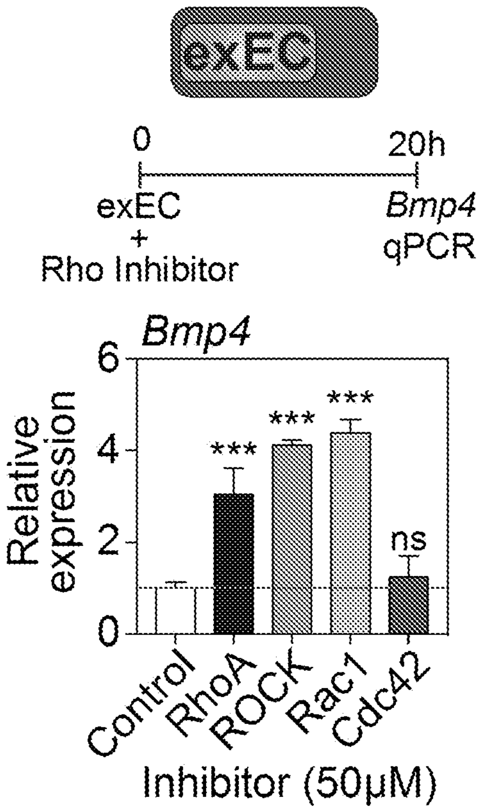
Figure 7B:
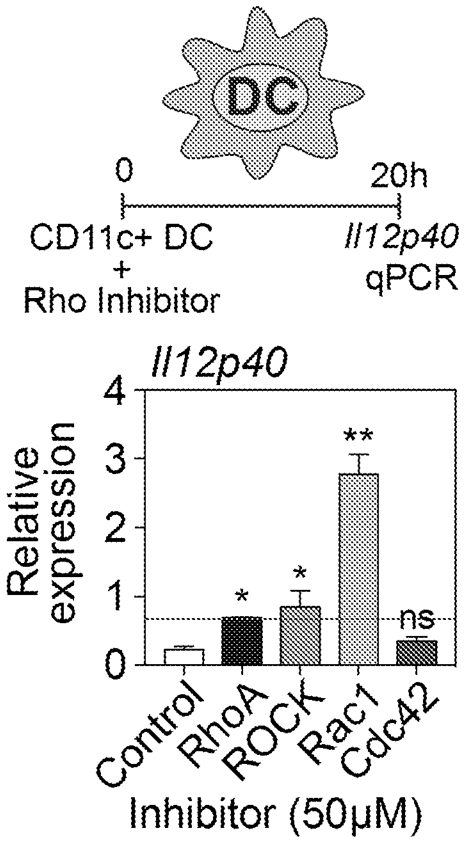

FIGS. 7A, 7B. Rho GTPase inhibition, using several small molecule inhibitors, promotes the expression of Bmp4 and the Il12p40 subunit of IL-23. Ex-vivo ECs (exECs) were generated from FACS purified ECs from the thymus and transduced with lentivirus containing the adenoviral gene E4orf1, as described here *Proc Natl Acad Sci USA*. 2008 Dec. 9; 105(49):19288-93. The exECs were cultured in Advanced DMEM-F12 (Gibco Life Technologies 12634-028) with 20% FBS, 10 mM HEPES buffer, 1% Glutamax (Life Technologies 35050061), 1% Pen Strep, 1% Non-Essential Amino Acids (Life Technologies 11140050), 50 μg/ml Endothelial cell supplement (Alfa Aesar J64516, BT-023), 5 μM SB431542 (R&D Systems 1614), 20 ng/ml FGF (Peprotech 100-18B), 10 ng/ml VEGF (Peprotech 450-32) at 37° C., 5% $O_2$ and 5% $CO_2$. Thymic dendritic cells (DCs) were obtained from the thymus of 6 week old C57BL/6 mice, where post enzymatic digestion CD11c+ cells were isolated using magnetic beads (Miltenyi Biotech 130-108-338), and cultured in DMEM plus 10% FBS and 1% PenStrep at 37° C., 21% $O_2$ and 5% $CO_2$. The exECs and DCs were separately treated with 50 μM of the individual Rho GTPase inhibitors: RhoA (Millipore/Sigma, Rhosin, CAS 1173671-63-0, 555460-25MG), ROCK (TC-S 700, Tocris, 4961), Rac1,2,3 (Tocris, EHT 1864, 2161), and Cdc42 (Millipore/Sigma, CDC42 Inhibitor III, ZCL278, 500503) for 20 h overnight before being lysed and prepared for RNA extraction. Bmp4 and Il-12p40 expression were determined by qPCR (exECs, n=3-6 wells from 2 separate experiments; DCs, n=3 mice).

(7A) Bmp4 and (7B) iI-12p40 expression was significantly upregulated in RhoA, ROCK and Rac1,2,3 inhibited exECs and DCs, respectively.

Figure 8:
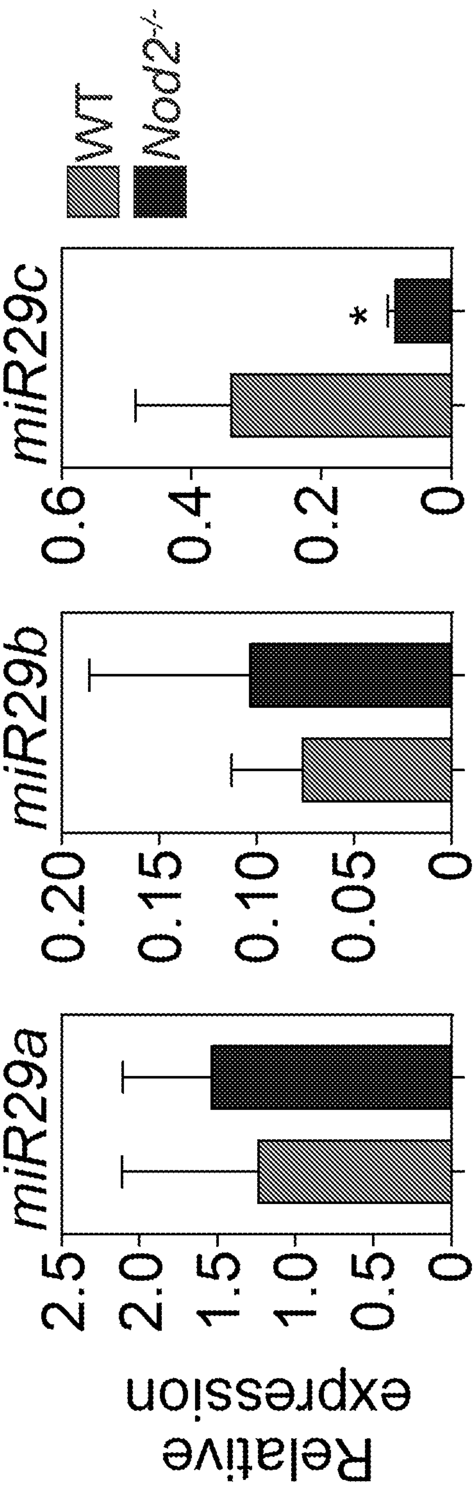

FIG. 8. Thymic miR29c expression is regulated by NOD2. The thymus from 6 week old C57BL/6 mice and 6 week old Nod2$^{-/-}$ mice were harvested at day 3 after TBI and prepared for RNA extraction (n=2-3 mice). cDNA was prepared from isolated RNA using the Taqman Advanced miRNA cDNA Synthesis kit (Thermo Fisher A28007), and relative miR29a, miR29b and miR29c expression was assessed by qPCR (primers from Thermo Fisher A25576).

miR29c expression is reduced in the Nod2-deficient thymus following TBI, compared with WT counterparts, whereas, miR29a and miR29b expression remains relatively similar to that of WT counterparts.

Figure 9:
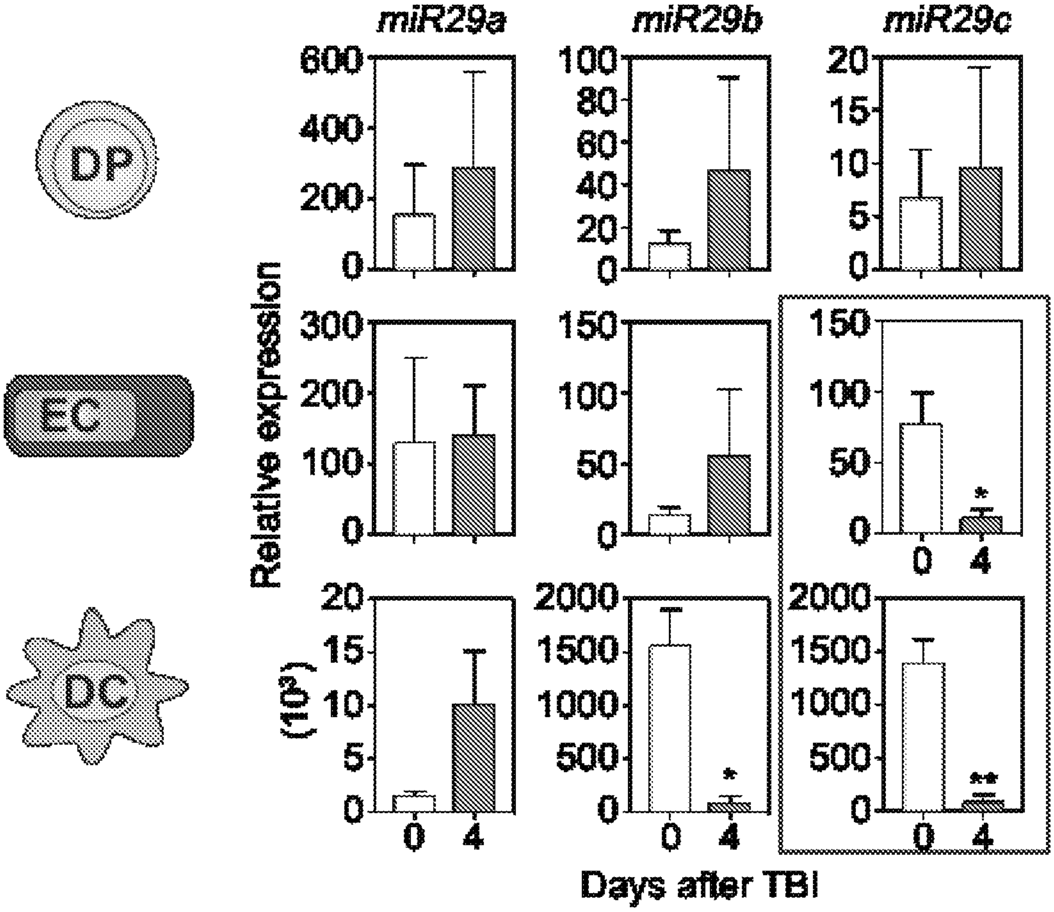

FIG. 9. Reduced miR29c expression in ECs and DCs after TBI. The thymus from 6 week old C57BL/6 mice were harvested at day 0 and day 4 after TBI and digested as described in FIG. 1 above. ECs, DCs and DP thymocytes were FACs sorted and prepared for RNA extraction. cDNA was prepared from isolated RNA using the Taqman Advanced miRNA cDNA Synthesis kit (Thermo Fisher A28007), and relative miR29a, miR29b and miR29c expression was assessed by qPCR (primers from Thermo Fisher A25576).

Expression analysis of miR29 family members, which have previously been shown to be induced downstream of NOD2 signaling, reveals reduced levels of miR29c in ECs and DCs at day 4 following TBI compared with day 0, as highlighted in the box.

Figure 10A:
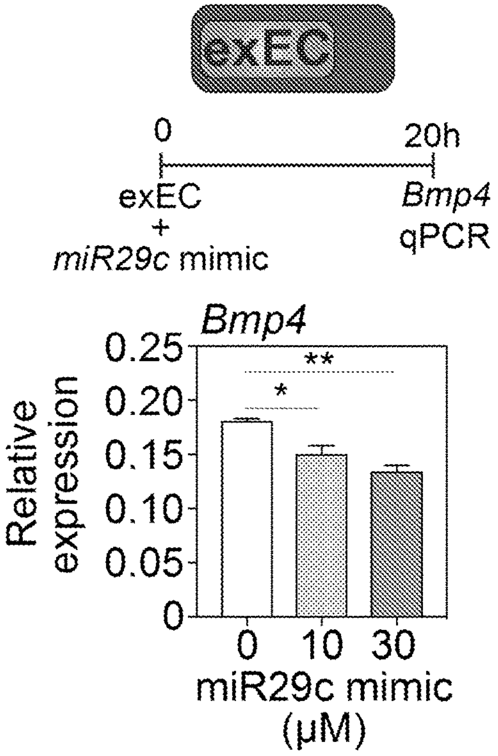
Figure 10B:
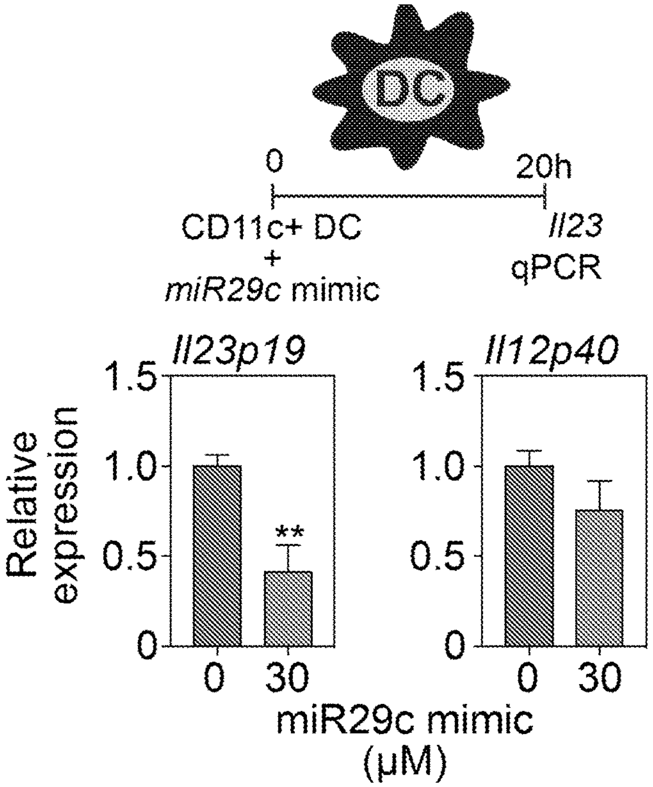

FIGS. 10A, 10B: In vitro treatment with a synthetic miR29c mimic reduces the expression of Bmp4 & IL-23, in ECs and DCs, respectively. exECs and DCs were generated and maintained as described in FIGS. 7A, 7B. 10 μM or 30 μM of miR29c mimic (Thermo Fisher, 4464066) was added to the culture media and cells were incubated for 20 h before lysis and preparation for RNA extraction. Bmp4 and IL-23 expression were determined by qPCR (n=3).

(10A) Bmp4 and (10B) IL-23 expression was significantly reduced in ECs and DCs, respectively, treated with the miR29c mimic.

Figure 11:
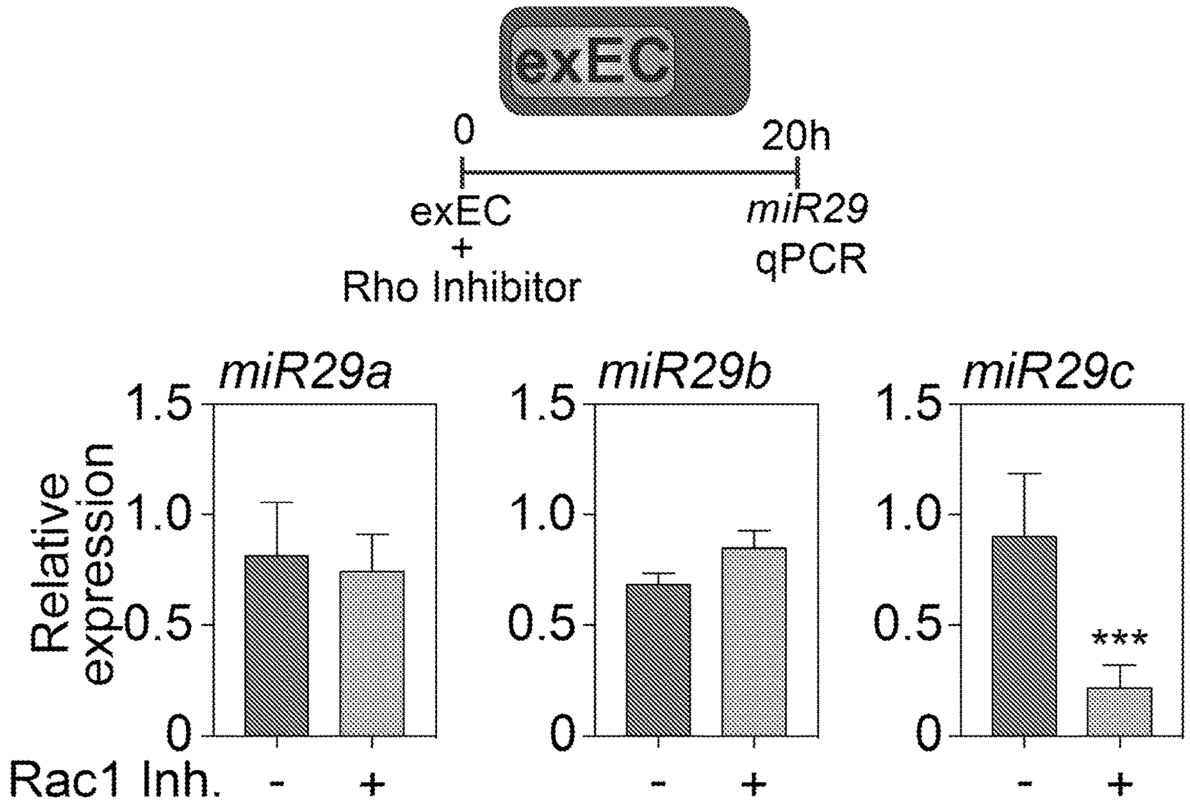

FIG. 11. miR29c expression is reduced after Rac1 inhibition in ECs. exECs were treated with 50 μM Rac1,2,3 (Tocris, EHT 1864, 2161) inhibitor as described in FIGS. 7A, 7B. cDNA was prepared from isolated RNA using the Taqman Advanced miRNA cDNA Synthesis kit (Thermo Fisher A28007), and relative miR29c expression was assessed by qPCR (primers from Thermo Fisher A25576).

miR29c expression is significantly reduced in exECs treated with the Rac1,2,3 inhibitor EH 1864, compared with untreated, supporting that Rho GTPase signals through NOD2. Notably, miR29a and miR29b levels were not reduced.

Figure 12:
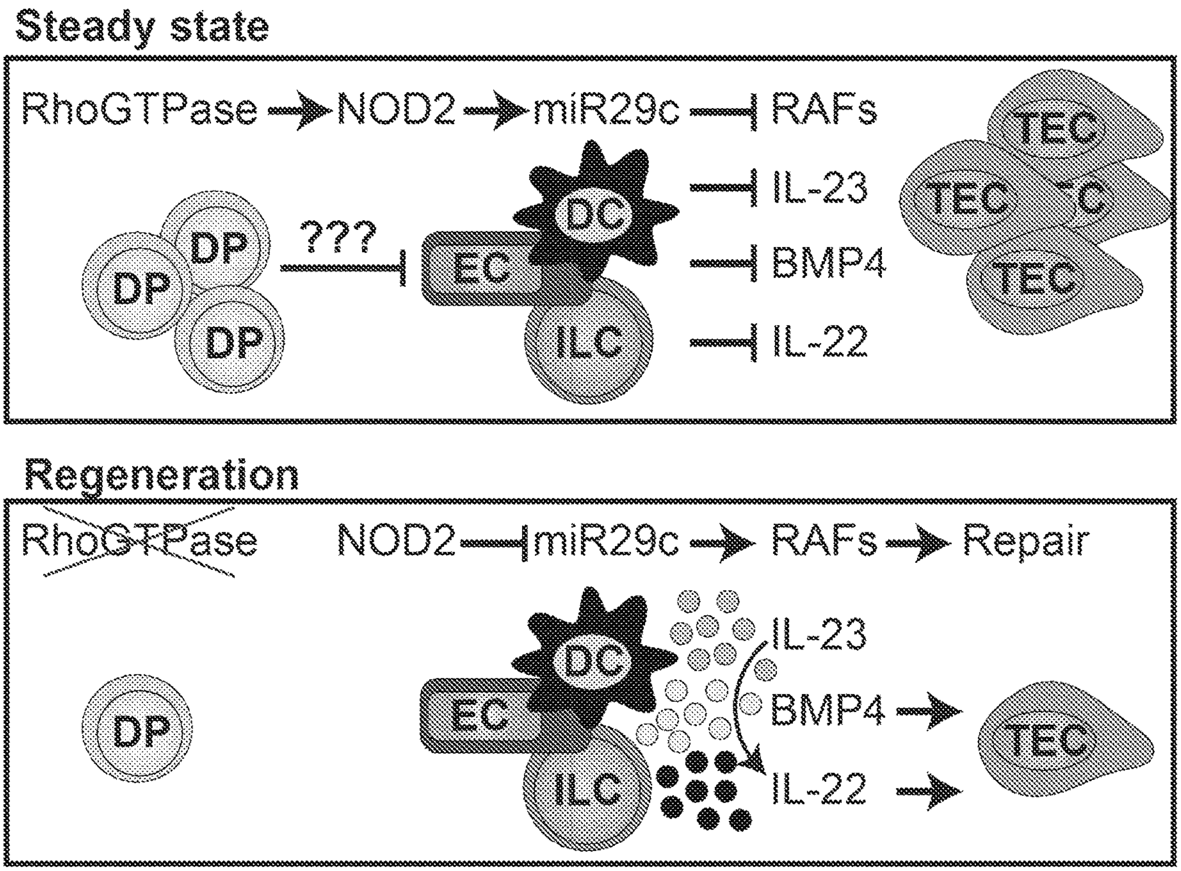

FIG. 12: Strategy to enhance thymic regeneration after damage by inhibiting Rho GTPases which limit NOD2-mediated suppression of the regeneration-associated factors BMP4, IL-23 and IL-22.

FIG. 13. Reference sequences supporting the disclosure.

DETAILED DESCRIPTION

The thymus is the primary site of T cell development and is extremely sensitive to damage, while concurrently possessing a remarkable regenerative capacity. Endogenous thymic regeneration is a crucial function that allows for renewal of immune competence following stress, infection and cytotoxic cancer treatments. Although there is continual thymic involution and regeneration in response to stress and infection in otherwise healthy people, prolonged T cell deficiency is common after profound thymic damage, such as that caused by the conditioning required for hematopoietic stem cell transplant.

Previous studies have revealed two pathways important for thymic regeneration, centered around the production of interleukin (IL)-22 and bone morphogenetic protein 4 (BMP4) by innate lymphoid cells (ILCs) and endothelial cells (ECs), respectively. Together these pathways provide novel therapeutic targets to induce regeneration in patients whose thymus has been damaged due to, for example, age, infection, or common cancer therapies such as chemotherapy and irradiation. Although these two pathways are crucial for endogenous thymic regeneration, the specific molecular mechanisms by which the pathways are triggered have been poorly understood. Here, the unexpected role for the cytoplasmic pattern recognition innate immune receptor nucleotide-binding oligomerization domain-containing protein 2 (NOD2) in governing multiple pathways of thymic regeneration is disclosed. Mice deficient for NOD2 show increased intrathymic levels of IL-22, IL-23, and BMP4 and increased thymus cellularity at baseline and after thymic damage caused by total body irradiation (TBI). Consistent with its regulation of these multiple regenerative pathways, NOD2 expression in ECs decreases following TBI, but increases in CD4+CD8+ thymocytes, demonstrating a cell-specific role of NOD2.

Although the canonical ligands of NOD2 signaling are bacterial, several non-bacterial regulators have been recently identified, including downstream components of mitochondrial and cellular stress pathways such as ATP and the Rho GTPase RhoA, even in the absence of pattern recognition. Inhibition of the Rho GTPases, RhoA and Rac1 can induce the production of BMP4 by ECs in vitro, and after TBI there is a significant reduction in these two Rho GTPases. Intracellular ATP levels are increased after damage in nod2−/− mice, and ATP induces BMP4 expression in ECs in an NF-kB independent manner. Furthermore, inhibition of RhoA, which can activate NOD2 independent of bacterial ligand, promotes the expression of BMP4 in ECs. A role for microRNA 29c (miR29c) is also shown by the data presented herein.

These studies not only enhance understanding of endogenous tissue regeneration, but also identify master regulators of multiple regeneration pathways, and reveal therapeutic strategies to boost thymic function in patients whose immune system has been damaged due to, for example, age, infection, or cancer therapies.

Without being bound by theory, the following principles are thought to underly the current disclosure: EC-derived BMP4 promotes thymic regeneration; NOD2 negatively regulates thymic cellularity and levels of pro-survival factors following TBI; nod2 expression and Cyt-c levels are reduced in ECs and increased in CD4+CD8+ thymocytes following TBI; mitochondrial dysfunction is reduced in ECs and increased in CD4+CD8+ thymocytes following TBI; inhibition of RhoA and Rac proteins (e.g., Rac1) result in increased expression of bmp4 in ECs.

The following disclosure provides additional description regarding: (I) NOD2 and Exemplary Inhibitors; (II) Rho GTPases and Exemplary Inhibitors; (Ill) miR29c and Exemplary Inhibitors; (IV) Use of RNA Interference to Inhibit NOD2, Rho GTPases, and/or miR29c; (V) Compositions; and (VI) Methods of Use.

(I) NOD2 and Exemplary Inhibitors. Nucleotide oligomerization domain (NOD) 2/Caspase activation and recruitment domain (CARD) 15 belongs to the described family of intracellular NOD-like receptor proteins (NLRs), which contain a central nucleotide-binding site domain flanked on its C-terminal side by a leucine-rich repeat domain and on its N-terminal side by two CARD domains. The NOD2 protein plays an important role in immune system function. The NOD2 protein is indeed expressed and active in monocytes and macrophages, and in dendritic cells. The protein is also active in several types of epithelial cells, including Paneth cells, which are found in the lining of the intestine. These cells help defend the intestinal wall against bacterial infection.

The NOD2 protein has several critic-al recognized functions in immune defense against foreign invaders. The protein is a cytosolic sensor for a conserved bacterially derived structure, namely Muramyl di-peptide (N-acetylmuramyl-L-Alanyl-D-Isoglutamine or MDP) and is capable of activating in response to proinflammatory signaling pathways, such as the NF-κB pathway. This protein complex regulates also the activity of multiple other genes, involved in control of immune responses and inflammatory reactions. FIG. 13 provides an exemplary protein sequence of NOD2, as well as other proteins described herein (SEQ ID NOs: 1-7).

Inhibitors of NOD2 can include ponatinib, regorafenib, and gefitinib which are multikinase inhibitors that target RIP2 kinase which forms a complex with NOD2 (Canning, et al. Chem Biol., 2015, 22, 1174-1184; Jakopin, *Med Chem.*, 2014, 57, 6897-6918). The structures of ponatinib, regorafenib, and gefitinib respectively include:

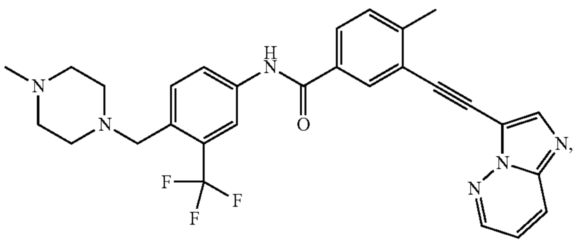

,

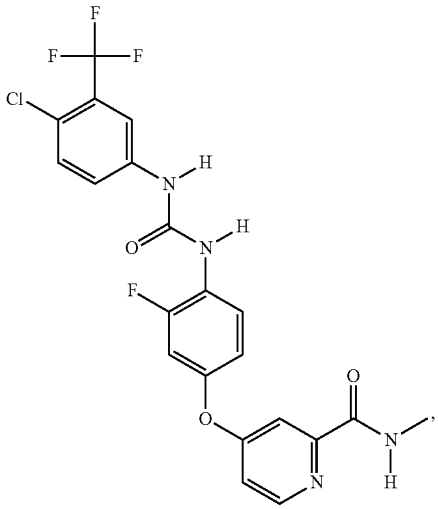

, and

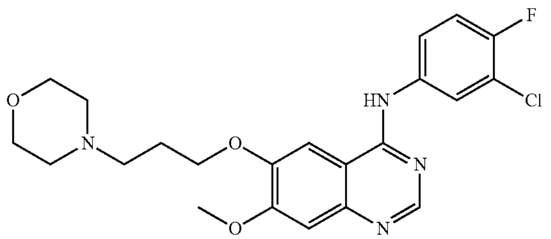

Additional inhibitors of NOD2 can include natural or endogenous compounds such as: Curcumin, a polyphenol from the plant *Curcuma longa*; sesquiterpene lactones such as parthenolide and helenalin; Pseudopterosins, such as pseudoterosin A, which are diterpenoid glycosides of marine origin; and polyunsaturated fatty acids such as docosahexaenoic acid (DHA) and eicosapentaenoic acid (EPA). These structures are shown below:

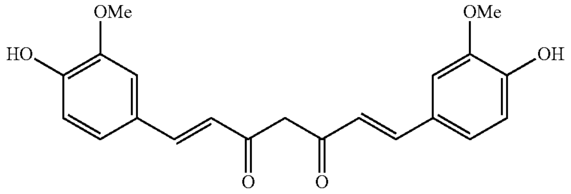
curcumin
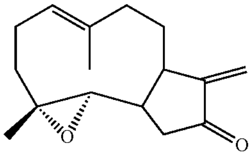
parthenolide
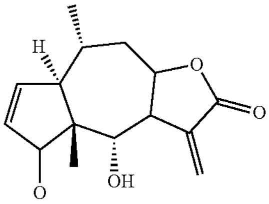
helenalin
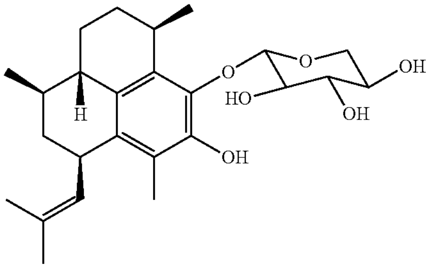
pseudopterosin A
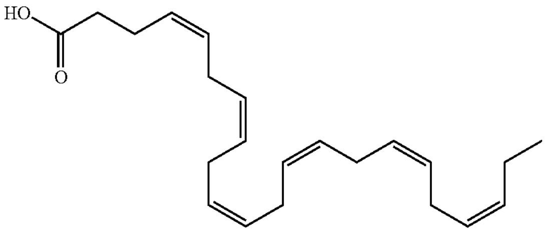
DHA-docosahexaenoic acid
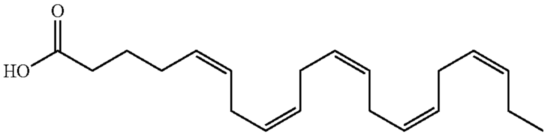
EPA-eicosapentaenoic acid
Inhibitors of NOD2 can further include benzimidazole diamides, representative structures of which are shown below:
GSK669
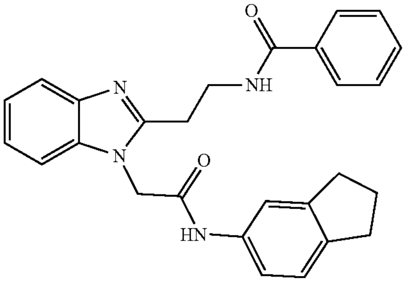
$IC_{50}$ (NOD2) = 3.3 μM
-continued
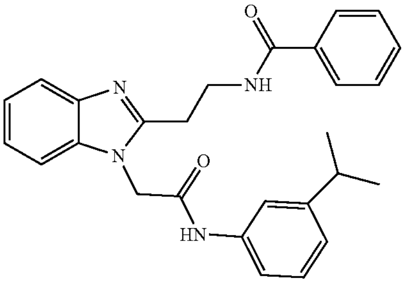
$IC_{50}$ (NOD2) = 0.8 μM
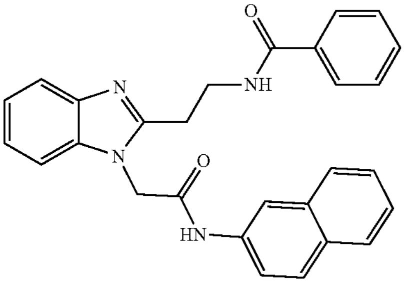
$IC_{50}$ (NOD2) = 1.6 μM
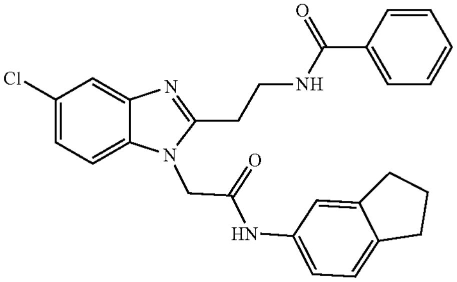
$IC_{50}$ (NOD2) = 1.3 μM
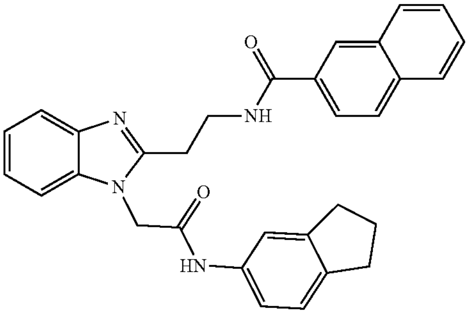
$IC_{50}$ (NOD2) = 3.4 μM
GSK717
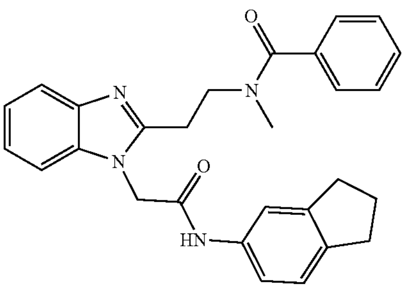
$IC_{50}$ (NOD2) = 0.4 μM -continued

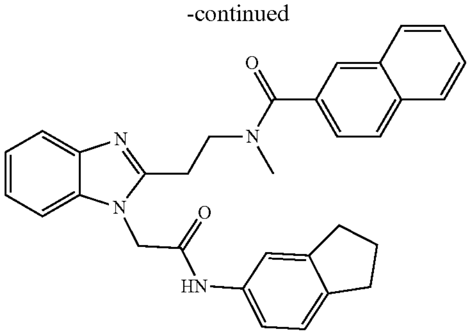

$IC_{50}$ (NOD2) = 0.2 μM

GSK717 NOD2 Signaling Inhibitor II is commercially available from Millipore Sigma (Cat #533718, Burlington, MA).

Inhibitors of NOD2 can further include hydrophenalene-chromium complexes, representative structures of which are shown below:

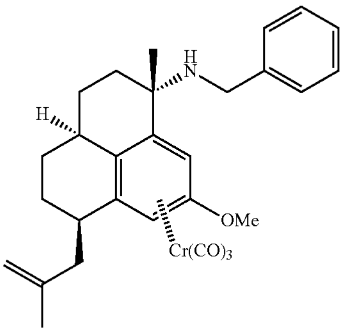

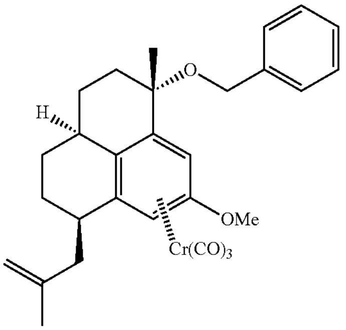

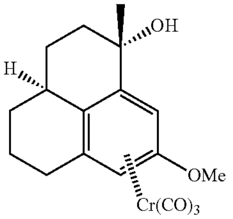

Additional inhibitors of NOD2 are disclosed in, for example, Jakopin Z (2014) Journal of Medicinal Chemistry 57(16): 6897-6918 and Rickard D J et al. (2013) PLoS ONE 8(8): e69619.

(II) Rho GTPases and Exemplary Inhibitors. Rho GTPases are small, membrane-bound, Ras-related GTP-binding proteins that function by binding and hydrolyzing GTP. Rho GTPases function as molecular switches, cycling between an inactive GDP-bound conformation and an active GTP-bound conformation. Rho GTPases can control endothelial cell Nitric Oxide Synthase activity.

Rho GTPases of the Ras superfamily are involved in the regulation of multiple cell functions and have been implicated in the pathology of various human diseases including cancers (Fritz et al., *Int. J. Cancer,* 1999, 81, 682-687; Fritz & Kaina, *Curr. Cancer Drug Targets,* 2006, 6, 1-14; Sahai & Marshall, *Nat. Rev. Cancer,* 2002, 2, 133-42), pathological angiogenesis such as in diabetic retinopathy, tumoral angiogenesis, glaucoma, and age-related macular degeneration (Eriksson et al., *Circulation,* 2003, 107, 1532-8; Soga et al., *Exp. Cell. Res.,* 2001, 269, 73-87; Fryer & Field, *Cancer Lett.,* 2005, 229, 13-23), asthma, Alzheimer's disease (Désiré et al., *J. Biol. Chem.,* 2005, 280(45), 37516-25), and cardiac left ventricular hypertrophy (Brown et al., *Circ Res.,* 2006, 98, 730-42; Molkentin & Dorn, 2nd *Annu Rev Physiol.* 2001, 63, 391-426).

Rho family proteins constitute one of three major branches of the Ras superfamily. Rho proteins share 30% amino acid identity with the Ras superfamily proteins. At least 14 mammalian Rho family proteins have been identified, including RhoA, RhoB, RhoC, RhoE/Rnd3, Rnd1/Rho6, Rnd2/Rho7, RhoG, Rac1, Rac1b, Rac2, Rac3, Cdc42, TC10, and TTF.

RhoA is a protein that is involved in a diverse set of signaling pathways including the ultimate regulation of the dynamic organization of the cytoskeleton. The first known biological function of RhoA, described in Swiss 3T3 fibroblasts, was the formation of stress fibers (actin filament bundles) and focal adhesion complexes upon the addition of extracellular ligands (Ridley, Int. J. Biochem. Cell Biol., 1997, 29, 1225-1229), These structures allow the cell to attach and pull along an extracellular substrate altering the cell's shape and position. Since then, the assembly of the cytoskeleton through the activation of RhoA has been demonstrated in epithelial cells, endothelial cells, astrocytes, lymphocytes, preadipocytes, platelets and neurons. While RhoA activation of cytoskeletal assembly most often results in the growth or extension of a cell, in neurons, RhoA can induce neurite retraction and cause cell rounding, (Hall, Science, 1998, 279, 509-514).

RhoA can also mediate actin-independent signaling cascades. These include 0) gene expression by activation of the serum response factor (SRF) which, along with ternary complex factors (TCFs), interacts with serum response elements found in certain gene promoters like c-fos, (ii) cell cycle progression through $G_1$ phase and (iii) induction of tumorigenic transformation of NIH 3T3 and Rat1 rodent fibroblasts (Khosravi-Far et al., Adv. Cancer Res., 1998, 72, 57-107).

RhoA is also believed to be involved in the development of cancer. Cellular transformation and acquisition of the metastatic phenotype are the two main changes normal cells undergo during the progression to cancer. Recent studies demonstrate that RhoA-regulated pathways can induce both changes in cells. Injecting cells transformed with rhoA genes directly into the bloodstream of mice produced metastasis, or tumor growth, in distant organs (del Peso et al., Oncogene, 1997, 15, 3047-3057).

Rac proteins (Rac1, 1b, 2, 3) act as molecular switches cycling between an active GTP-bound and an inactive GDP-bound form through nucleotide exchange and hydrolysis. Like most other GTPases, these proteins adopt different conformations depending on the bound nucleotide, the main differences lying in the conformation of two short and flexible loop structures designated as the switch I and switch II regions. The three distinct mammalian Rac isoforms, Rac 1, 2 and 3, share a very high sequence identity (up to 90%), with Rac1b being an alternative splice variant of Rac1 with a 19 amino add insertion in vicinity to the switch II region. Rac1b has an accelerated GEF-independent GDP/GTP-exchange and an impaired GTP-hydrolysis, accounting fora self-activating GTPase (Haeusler et al., *Methods in Enzymology,* 2006, 406, 1-11).

Rac1 regulates the activity of the superoxide anion generating NADPH oxidase system of phagocytes, plays a central role in organization of the actin cytoskeleton, and is essential for Ras-induced transformation. In addition, mutant, constitutively active Rac1b can induce cellular transformation, invasion, and metastasis. Similar to Ras proteins, Rac1 is activated by upstream Guanine nucleotide Exchange Factors (GEFs) and binds effector proteins that signal downstream. Human cells contain 3 homologous Rac proteins, Rac1, Rac2, and Rac3, that are essentially identical except for the hypervariable C-terminal domains. Rac1, but not Rac2 or Rac3, contains a polybasic domain within its hypervariable region that is virtually identical to the polybasic domain of K-Ras 4B.

Rac1 binds to and activates the effector protein PAK1 more efficiently than Rac2 does, and the polybasic domain of Rac1 accounts for the enhanced ability of Rac1 to bind to and activate PAK1 (Knaus et al., *J. Biol. Chem.,* 1998, 273, 21512). The polybasic domain is also crucial for Rac1 mediated activation of NADPH oxidase and membrane ruffling but is not required for Rac1 mediated cell transformation or binding of Rac1 to the effector protein PORI (Jones & Jackson, *J. Biol. Chem.,* 1998, 273, 1782).

Inhibitors of Rho GTPases, such as RhoA and Rac1 can include: isoflavones such as genistein, daidzein, and glycitein (Seok et al. (2008) Journal of Pharmacology and Experimental Therapeutics 326(3): 991-998); 2-substituted quinoline (or quinoxaline) derivatives such as (E)-3-(3-(ethyl(quinolin-2-yl)amino)phenyl)acrylic acid and (E)-3-(3-(butyl(quinolin-2-yl)amino)phenyl)acrylic acid (Ma et al. (2015) ChemMedChem 10(1): 193-206); C3 transferase covalently linked to a proprietary cell penetrating moiety via a disulfide bond (Cat #CT03, Cytoskeleton Inc., Denver, CO); BA-210 (Cethrin® (BioAxone BioSciences Inc., Cambridge, MA), a recombinant fusion protein composed of C3 enzyme (Lord-Fontaine et al. (2008) J Neurotrauma 25: 1309-1322); ZCL 278 or 2-(4-Bromo-2-chlorophenoxy)-N-[[[4-[[(4,6-dimethyl-2-pyrimidinyl)amino]sulfonyl]phenyl] amino] thioxomethyl] acetamide, Cdc42 inhibitor (Cat #4794, Tocris, Minneapolis, MN); Rhosin hydrochloride or D-Tryptophan (2E)-2-(6-quinoxalinylmethylene)hydrazide hydrochloride, Rho GTPase inhibitor (Cat #5003, Tocris, Minneapolis, MN; Shang et al. (2012) Chemistry & Biology 19: 699-710); ML 141 or 4-[4,5-Dihydro-5-(4-methoxyphenyl)-3-phenyl-1H-pyrazol-1-yl]benzenesulfonamide, selective inhibitor of Cdc42 Rho family GTPase (Cat #4266, Tocris, Minneapolis, MN; Hong et al. (2013) J Biol Chem 288(12): 8531-8543); CASIN, Cdc42 inhibitor (Florian et al. (2012) Cell Stem Cell 10: 520-530); p120 catenin, a RhoA inhibitor (Anastasiadis (2000) Nature Cell Biology 2: 637-644); MLS000532223, Rho family GTPase inhibitor (Surviladze et al. (2010) J Biomolecular Screening 15(1): 10-20); and MLS000573151, Cdc42 inhibitor (Surviladze et al. (2010), supra). Small molecule RhoA inhibitors are further disclosed in Deng et al. (2011) J Med Chem 54(13): 4508-4522.

Inhibitors of Rac GTPases. Inhibitors of Rac GTPases can particularly include: EHT 1864 (5-(5-(7-(Trifluoromethyl) quinolin-4-ylthio)pentyloxy)-2-(morpholinomethyl)-4H-pyran-4-one dihydrochloride, a potent inhibitor of Rac family GTPases including Rac1, Rac1b, Rac2, and Rac3 (Cat #3872, Tocris, Minneapolis, MN)); Rac1 Inhibitor W56 (MVDGKPVNLGLWDTAG, SEQ ID NO: 8), a peptide including residues 45-60 of the guanine nucleotide exchange factor (GEF) recognition/activation site of Rac1 that selectively inhibits Rac1 interaction with Rac1-specific GEFs TrioN, GEF-H1 and Tiam1 (Cat #2221, Tocris, Minneapolis, MN); NSC 23766 or $N^6$-[2-[[4-(Diethylamino)-1-methylbutyl]amino]-6-methyl-4-pyrimidinyl]-2-methyl-4,6-quinolinediamine trihydrochloride, selective inhibitor of Rac1-GEF interaction (Cat #2161, Tocris, Minneapolis, MN; Gao et al. (2004) PNAS USA 101: 7618-7623); EHop 016 or $N^4$-(9-Ethyl-9H-carbazol-3-yl)-$N^2$-[3-(4-morpholinyl)propyl]-2,4-pyrimidinediamine, Rac inhibitor (Cat #6248, Tocris, Minneapolis, MN; Montalvo-Ortiz et al. (2012) J Biol Chem 287(16): 13228-13238); and 6-mercaptopurine (6-MP) and its derivative 6-thioguanosine-5'-triphosphate (6-T-GTP) (Marinkovic et al. (2014) J Immunol 192(9): 4370-4378).

(III) miR29c and Exemplary Inhibitors. miRNA or miR refers to a non-coding RNA between 18 and 25 nucleobases in length which hybridizes to and regulates the expression of a coding RNA. In certain embodiments, a miRNA is the product of cleavage of a pre-miRNA by the enzyme Dicer. Examples of miRNAs are found in the miRNA database known as miRBase.

In particular embodiments, miR29c refers to Accession No. MIMAT0000536 (UAGCACCAUUUGAAAUCGGUUA (SEQ ID NO: 9)). In particular embodiments, miR29c refers to Accession No. MIMAT0004632 (UGACCGAUUUCUCCUGGUGUUC (SEQ ID NO: 10)). In particular embodiments, miR29c refers to UAGCACCAUUUGAAAUCGGU (SEQ ID NO: 11). For additional information regarding miR29c, see, for example, WO2008154098; Lagos-Quintana et al., Curr Biol. 12:735-739 (2002); Poy et al., Nature. 432:226-230 (2004); Landgraf et al., Cell. 129:1401-1414 (2007); Ahn et al., Mol Hum Reprod. 16:463-471 (2010); and Chiang et al., Genes Dev. 24:992-1009 (2010).

In particular embodiments, an inhibitor of miR29c includes an antisense compound targeted to miR29c. In particular embodiments, an inhibitor of miR29c includes a modified oligonucleotide having a nucleobase sequence that is complementary to miR29c or a precursor thereof. In particular embodiments, an inhibitor of miR29c can be mmu-miR-29c-5p (AUCUCUUACACAGGCUGACCGAUUUCUCCUGGUGUUCAGAGUCUGUUUUUGUCUAGCA CCAUUUGAAAUCGGUUAUGAUGUAGGGGGA (SEQ ID NO: 12)). Inhibitors of miR29c can also include other small molecules or compounds such as PPAR-γ agonists including pioglitazone, 15-deoxy-delta-12,14-$PGJ_2$ or a thiazolidinedione.

(IV) Use of RNA Interference to Inhibit NOD2, Rho GTPases, and miR29c. In particular embodiments, inhibition of NOD2, Rho GTPases, and/or miR29c can be achieved through RNA interference and/or by genetic modification.

RNA interference (RNAi) refers to the process of sequence-specific post-transcriptional gene silencing in animals mediated by short interfering RNAs (siRNAs) (Fire et al. (1998) Nature 391:806-810). RNAi may have evolved in response to the production of double-stranded RNAs (dsRNAs) derived from viral infection or from the random integration of transposon elements into a host genome via a cellular response that specifically destroys homologous single-stranded RNA of viral genomic RNA.

The presence of long dsRNAs in cells stimulates the activity of Dicer, a ribonuclease III enzyme. Dicer is involved in the processing of the dsRNA into siRNAs (Bernstein et al. (2001) Nature 409:363-366). Short interfering RNAs derived from dicer activity are typically 21 to 23 nucleotides in length and include 19 base pair duplexes (Elbashir et al. (2001) Genes Dev 15:188-200). Dicer has also been implicated in the excision of 21- and 22-nucleotide small temporal RNAs (stRNAs) from precursor RNA of conserved structure that are implicated in translational control (Hutvagner et al. (2001) Science 293:834-838). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir et al. (2001) Genes Dev 15:188-200). In addition, RNA interference can also involve small RNA (e.g., microRNA, or miRNA) mediated gene silencing, presumably through cellular mechanisms that regulate chromatin structure and thereby prevent transcription of target gene sequences (see, e.g., Allshire, Science 297:1818-1819 2002; Volpe et al. (2002) Science 297:1833-1837; Jenuwein (2002) Science 297: 2215-2218; Hall et al. (2002) Science 297:2232-2237).

Based on the foregoing, miRNA molecules can be used to mediate gene inhibition via interaction with RNA transcripts or alternately by interaction with particular gene sequences, wherein such interaction results in gene inhibition either at the transcriptional or post-transcriptional level. RNAi has been studied in a variety of systems. For more information, see, for example, Fire et al. ((1998) Nature 391:806-811); Wianny and Goetz ((1999) Nature Cell Biol 2:70); Hammond et al. ((2000) Nature 404:293-296); and Elbashir et al. ((2001) Nature 411:494-498).

Nucleic acid sequences encoding and/or interfering with proteins disclosed herein can be derived by those of ordinary skill in the art based on well-known publicly available databases. Of most importance to the current disclosure is that there be enough sequence complementarity to mediate targeted gene inhibition, which can be assessed using assays disclosed herein.

(V) Compositions. Compounds or molecules that inhibit NOD2, Rho GTPases and/or miR29c as disclosed herein can be formulated into compositions for administration to subjects. Compositions include an inhibitory compound as described herein and a pharmaceutically acceptable carrier. Inhibitory compounds can also include pharmaceutically acceptable salts, tautomers, isomers, and prodrugs of inhibitory compounds described herein.

Exemplary pharmaceutically acceptable salts include acetate, acid citrate, acid phosphate, ascorbate, benzenesulfonate, benzoate, besylate, bisulfate, bitartrate, bromide, chloride, citrate, ethanesulfonate, formate, fumarate, gentisinate, gluconate, glucaronate, glutamate, lactate, methanesulfonate, nitrate, iodide, isonicotinate, maleate, oleate, oxalate, p-toluenesulfonate, pamoate (i.e., 1,1'-methylene-bis-(2-hydroxy-3-naphthoate)), pantothenate, phosphate, saccharate, salicylate, succinate, sulfate, tannate and tartrate salts.

"Prodrugs" refer to compounds that can undergo biotransformation (e.g., either spontaneous or enzymatic) within a subject to release, or to convert (e.g., enzymatically, mechanically, electromagnetically, etc.) an active or more active form of a compound after administration. Prodrugs can be used to overcome issues associated with stability, toxicity, lack of specificity, or limited bioavailability and often offer advantages related to solubility, tissue compatibility, and/or delayed release (See e.g., Bundgard, Design of Prodrugs, pp. 7-9, 21-24, Elsevier, Amsterdam (1985); and Silverman, The Organic Chemistry of Drug Design and Drag Action, pp. 352-401, Academic Press, San Diego, CA (1992)).

Pharmaceutically acceptable carriers include those that do not produce significantly adverse, allergic or other untoward reactions that outweigh the benefit of administration, whether for research, prophylactic and/or therapeutic treatments. Exemplary pharmaceutically acceptable carriers and formulations are disclosed in Remington's Pharmaceutical Sciences, 18th Ed. Mack Printing Company, 1990. Moreover, compositions can be prepared to meet sterility, pyrogenicity, general safety and purity standards as required by United States FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

For injection, compositions can be made as aqueous solutions, such as in buffers such as Hanks' solution, Ringer's solution, or physiological saline. The solutions can contain formulatory agents such as suspending, stabilizing and/or dispersing agents. Alternatively, the composition can be in lyophilized and/or powder form for constitution with a suitable vehicle, e.g., sterile pyrogen-free water, before use.

For oral administration, the compositions can be made as tablets, pills, dragees, capsules, liquids, gels, syrups, slurries, suspensions and the like.

For administration by inhalation, compositions can be made as aerosol sprays from pressurized packs or a nebulizer, with the use of a suitable propellant, e.g., dichlorodifluoromethane, trichlorofluoromethane, dichlorotetrafluoroethane, carbon dioxide or other suitable gas.

Compositions can also be depot preparations. Such long acting compositions may be administered by, for example, implantation or injection. Thus, for example, compounds can be formulated with suitable polymeric or hydrophobic materials (for example as an emulsion in an acceptable oil) or ion exchange resins, or as sparingly soluble derivatives, for example, as sparingly soluble salts.

(VI) Methods of Use. Methods disclosed herein include promoting thymic regeneration. In particular embodiments, thymic regeneration is promoted by up-regulating IL-22, IL-23 and/or BMP4. In particular embodiments, IL-22, IL-23 and/or BMP4 are up-regulated by inhibiting NOD2, Rho GTPases (e.g., RhoA and/or Rac1), and/or miR29c.

Particular embodiments disclosed herein can include treating subjects. Subjects include humans, veterinary animals (dogs, cats, reptiles, birds, etc.) livestock (horses, cattle, goats, pigs, chickens, etc.) and research animals (monkeys, rats, mice, fish, etc.) with compositions disclosed herein. Treating subjects includes delivering therapeutically effective amounts. Therapeutically effective amounts include those that provide effective amounts, prophylactic treatments and/or therapeutic treatments.

An "effective amount" is the amount of a compound necessary to result in a desired physiological change in the subject. Effective amounts are often administered for research purposes. Effective amounts disclosed herein can cause a statistically-significant effect in an animal model or in vitro assay relevant to thymic function or regeneration.

A "prophylactic treatment" includes a treatment administered to a subject who does not display signs or symptoms of thymic damage or displays only early signs or symptoms of thymic damage such that treatment is administered for the purpose of diminishing or decreasing the risk of developing thymic damage further. Thus, a prophylactic treatment functions as a preventative treatment against thymic damage. In particular embodiments, prophylactic treatments reduce, delay, or prevent thymic damage.

A "therapeutic treatment" includes a treatment administered to a subject who displays symptoms or signs of thymic damage and is administered to the subject for the purpose of diminishing or eliminating those signs or symptoms of thymic damage. The therapeutic treatment can reduce, control, or eliminate the presence or activity of thymic damage and/or reduce control or eliminate side effects of thymic damage. In particular embodiments, therapeutic treatments reduce, delay, or prevent further thymic damage from occurring. In particular embodiments, therapeutic treatments lead to thymic regeneration. In particular embodiments, a therapeutic treatment results in an increase in T cells.

In particular embodiments, a therapeutic treatment ameliorates at least one symptom of a disorder associated with thymic insufficiency. In particular embodiments, a thymic insufficiency is evidenced by a reduced numbers of T cells, e.g., CD4+ T cells, and/or naive (CD45RA+CD62L+) T cells. In particular embodiments, a thymic insufficiency is evidenced by T cell levels that are persistently (e.g., over a period of weeks to months) below a threshold level, e.g., below 50, 100, 200, 300, 400, or 500 cells/$mm^3$ of whole blood; less than 50 naive T cells/$mm^3$; and/or naive T cells comprising less than 5% of total T cells by flow cytometry. Alternatively or in addition, thymic insufficiency can be diagnosed based on a low number of recent thymic emigrating T cells via PCR-based measurement of TCR-excision circles (e.g., as described in Geenen et al., (2003). J. Endocrinol. 176, 305-311).

In particular embodiments, administration of a therapeutically effective amount can result in increased thymic mass and increased levels of naive, newly developed T cells. In particular embodiments, a therapeutic treatment results in an increase in numbers of T cells, e.g., levels of CD4+ T cells, and/or levels of naive (CD45 RA+CD62L+) T cells, that are persistently (e.g., over a period of weeks to months) above a threshold level. The threshold level can be above 50, 100, 200, 300, 400, or 500 cells/$mm^3$ of whole blood. In particular embodiments, treatments disclosed herein result in more than 50 naive T cells/$mm^3$ and/or naive T cells that include more than 5% of total T cells by flow cytometry. Thus methods disclosed herein can include monitoring numbers of T cells, e.g., levels of CD4+ T cells, and/or levels of naive (CD45RA-t-CD62L+) T cells, or monitoring the numbers of recent thymic emigrating T cells via PCR-based measurement of T cell receptor rearrangement excision circles (Geenen et al., (2003). J. Endocrinol. 176, 305-311) and adjusting or continuing dosing until a threshold level is reached.

In particular embodiments, thymic insufficiency is associated with a chronic infection, such as a viral or bacterial infection. Over time, a therapeutic treatment can result in T cells recognizing the infectious agent causing the infection. In particular embodiments, a therapeutic treatment can result in an increase in the variety of epitopes recognized by the subject's T cells (i.e., a more diverse T cell repertoire). In particular embodiments, the infection is with Human Immunodeficiency Virus (HIV), hepatitis (e.g., Hepatitis C or Hepatitis B virus); subacute sclerosing panencephalitis (chronic measles encephalitis); chronic papovavirus encephalitis (progressive multifocal leukoencephalopathy); and/or Epstein-Barr virus infection.

In particular embodiments, the subject has been exposed to a toxin that affects thymic size or function, e.g., organotin compounds, glucocorticosteroids, 2,3,7,8-tetrachlorodibenzo-p-dioxin, or cyclosporine (see, e.g., Schuurman et al., int J Immunopharmacol. 1992 April; 14(3):369-75). In particular embodiments, the subject has cancer, and has been treated with a chemotherapeutic agent that is thymotoxic.

Toxicity or lesion in thymus has been reported in the following cancer treatments: pre-bone marrow transplantation conditioning, chemotherapy, radiotherapy (Heng et al., Curr Opin Pharmacol 10(4):425-33, 2010): cisplatin (Rebillard et al., Oncogene. 27(51):6590-5, 2008); cyclophosphamide (CPA) (Zusman et al., In Vivo. 16(6):567-76, 2002); NAVELBINE® (Pierre Fabre Medicament Joint Stock Company, Boulogne, France) i.v. Vinorelbine (Su et al., Int J Pharm. 411(1-2): 188-96, 2011); nucleoside-based analogues (Belinsky et al., Cancer Res, 67(1):262-8, 2007); fractionated low-dose radiation (Pogribny et al., Mol Cancer Res. 3(10):553-61, 2005); recombinant human IL-2 (rhIL-2) (Lee et al., Regul Toxicol Pharmacol. 64(2):253-62, 2012); CP-31398 (N'-[2-[2-(4-methoxyphenyl)ethenyl]-4-quinazolmyl]-N,N-dimethyl-1,3-propanediamine dihydrochloride), a styrylquinazoline that stabilizes the DNA binding conformation of p53 (Johnson et al., Toxicology. 289(2-3): 141-50, 2011); synthetic retinoic acid analog, 9-cis-UAB30 [(2E,4E,6Z,8E)-8-(3',4'-dihydro-1 '(2'H)-naphthalen-1'-ylidene)-3,7-dimethyl-2,4,6-octatrienoic acid], which is used to treat breast cancer (Kapetanovic, Int J Toxicol. 29(2): 157-64, 2010); flavopiridol, a cyclin-dependent kinase inhibitor, in treating non-small lung cancer (Zveleil, IDrugs. 1(2):241-6, 1998); E-41B (ethyl-4-isothiocyanatobutanoate) (Tulinska et al., Toxicology 145(2-3):217-25, 2000); 5-fluorouracil (5-FU) and its prodrug 5'-deoxy-5-fluorouridine (5'-DFUR) (Ishikawa et al., Jpn J Cancer Res. 80(6):583-91, 1989); and cyclosporine A (Bennett, J Natl Cancer Inst. 75(5):925-36, 1985), among others.

In particular embodiments, the subject has or is at risk of developing an autoimmune disease associated with or as a result of having a reduced numbers of T cells, or of an aberrant T cell repertoire; see, e.g., Datta and Sarvetnick, (2009) Trends Immunol 30, 430-438; Gagnerault, et al., (2009) The Journal of Immunology 183, 4913-4920; Kaminitz, et al., (2010). J Autoimmun 35, 145-152; King, et al., (2004) Cell 117, 265-277; and Zou et al. (2008) Eur J Immunol 38, 986-994.

In particular embodiments, the subject has experienced trauma to the thymic region or has had a surgical procedure that impacted the size of the thymus, e.g., cardiothoracic surgery (e.g., in neonates; see, e.g., Eysteinsdottir et al., Clin Exp Immunol. 2004 May; 136(2): 349-355). In particular embodiments, the subject has undergone a thymectomy, e.g., to treat cancer, e.g., thymoma, or to treat myasthenia gravis (Manlula et al., Chest 2005; 128:3454-3460).

For administration, therapeutically effective amounts (also referred to herein as doses) can be initially estimated based on results from in vitro assays and/or animal model studies. The actual dose amount administered to a particular subject can be determined by a physician, veterinarian or researcher taking into account parameters such as physical and physiological factors including target, body weight, severity of thymic damage, cause of thymic damage, stage of thymic damage, previous or concurrent therapeutic interventions, idiopathy of the subject and route of administration.

Useful doses can range from 0.01 to 500 μg/kg or from 0.01 to 500 mg/kg. Therapeutically effective amounts can be achieved by administering single or multiple doses during the course of a treatment regimen (e.g., daily, every other day, weekly, monthly, every 6 months, or yearly).

In particular embodiments, the methods described herein are employed in combination with one or more other treatment modalities, e.g., treatment modalities for the regeneration of the thymus or parts thereof, e.g., as described in Lynch, et al., (2009) Trends Immunol 30, 366-373. Exemplary methods include castration (Griffith et al., (2011) Aging Cell 11, 169-177); administration of keratinocyte growth factor (KGF; Min et al., (2007), Blood 109, 2529-2537); administration of ghrelin (Dixit et al., (2007). J Clin Invest 1 17, 2778-2790); administration of human growth hormone (Goya et al., (1992). Brain Behav. Immun. 6, 341-354); and administration of interleukin-22 (Dudakov et al., (2012). Science 336, 91-95) or BMP4 (US 20170292111). Thus the methods can include administering a NOD2, Rho GTPase, and/or miR29c inhibitor in combination with KGF, ghrelin, human growth hormone, and/or IL-22. e.g., administered simultaneously, e.g., in the same or different pharmaceutical composition and at substantially the same time (e.g., within 30-60 minutes of each other), or administered sequentially, e.g., in one or more doses.

In particular embodiments, the methods also include transplanting thymic tissues into a subject, e.g., where the subject lacks a thymus altogether, e.g., due to genetic reasons, e.g., DiGeorge syndrome, or as a result of other causes including those listed above. In particular embodiments, allogeneic thymic tissue is transplanted, e.g., as described in Markert et al., Clin Immunol. 2010 May; 135(2):236-46; Markert et al., N Engl J Med, 1999 Oct. 14:34 1 (16); 1180-9; Markert et al., Blood. 2004 Oct. 15; 104(8):2574-81; Markert et al., Blood. 2007 May 15; 109 (10):4539-47; and Chinn and Markert, J Allergy Clin Immunol 2011 June; 127(6): 1351-5. In particular embodiments, the transplant includes a thymic epithelial cell, or other thymic stromal cell or a stromal ceil derived from another tissue such as skin, or a hematopoietic thymic homing cell such as a common lymphoid progenitor cell or a multipotent progenitor cell (see, e.g., Boehm and Bleul, Trends in Immunology 27(10):477-484 (2006); Dunon and Imhof, Blood, 81 (1): 1-8 (1993); Zlotoff and Bhandoola, Annals of the New York Academy of Sciences, 1217 (Year in Immunology): 122-138 (2011)). In particular embodiments immune suppressive treatments are also administered, as described in the above references.

Exemplary Embodiments

1. A method of promoting thymic regeneration in a subject in need thereof including administering a therapeutically effective amount of a composition that inhibits Rho GTPases, NOD2, and/or miR29c to the subject thereby promoting thymic regeneration in the subject.
2. The method of embodiment 2, wherein the subject is in need of promoted thymic regeneration due to age, infection, and/or a cancer treatment.
3. The method of embodiment 1 or 2, wherein the compound that inhibits Rho GTPases includes isoflavones, (E)-3-(3-(ethyl(quinolin-2-yl)amino)phenyl) acrylic acid, (E)-3-(3-(butyl(quinolin-2-yl)amino)phenyl)acrylic acid, C3 transferase, ZCL 278, Rhosin hydrochloride, ML 141, CASIN, p120 catenin, MLS000532223, and/or MLS000573151.
4. The method of any of embodiments 1-3, wherein the Rho GTPases include RhoA and/or Rac1.
5. The method of embodiment 5, wherein the compound that inhibits Rac1 includes EHT 1864, Rac1 Inhibitor W56, NSC 23766, EHop 016, 6-mercaptopurine (6-MP), and/or 6-thioguanosine-5'-tri phosphate (6-T-GTP).
6. The method of any of embodiments 1-5, wherein the compound that inhibits NOD2 includes ponatinib, regorafenib, gefitinib, curcumin, a sesquiterpene lactone, a pseudopterosin, a polyunsaturated fatty acid, a benzimidazole diamide, and/or a hydrophenalene-chromium complex.
7. The method of any of embodiments 1-6, wherein the compound that inhibits NOD2 includes a sesquiterpene lactone selected from parthenolide and/or helenalin.
8. The method of any of embodiments 1-7, wherein the compound that inhibits NOD2 includes pseudopterosin A.
9. The method of any of embodiments 1-8, wherein the compound that inhibits NOD2 includes a polyunsaturated fatty acid selected from docosahexaenoic acid (DHA) and/or eicosapentaenoic acid (EPA).
10. The method of any of embodiments 1-9, wherein the compound that inhibits NOD2 includes a benzimidazole diamide selected from GSK669 and/or GSK717.
11. The method of any of embodiments 1-10, wherein the compound that inhibits miR29c includes a complementary interfering RNA sequence.
12. The method of any of embodiments 1-11, wherein the compound that inhibits miR29c includes SEQ ID NO: 12.
13. The method of any of embodiments 1-12, wherein the compound that inhibits miR29c includes a PPAR-γ agonist.
14. The method of embodiment 13, wherein the PPAR-γ agonist includes pioglitazone, 15-deoxy-delta-12,14-$PGJ_2$ and/or thiazolidinedione.
15. A method of upregulating IL-22, IL-23, and/or BMP4 in a subject in need thereof including administering a therapeutically effective amount of a composition that inhibits Rho GTPases, NOD2, and/or miR29c to the subject thereby upregulating IL-22, IL-23, and/or BMP4 in the subject.
16. A method of embodiment 15, wherein the upregulating promotes thymic regeneration in the subject.
17. The method of embodiment 15 or 16, wherein the subject has reduced thymic function due to age, infection, and/or a cancer treatment.
18. The method of any of embodiments 15-17, wherein the compound that inhibits Rho GTPases includes isoflavones, (E)-3-(3-(ethyl(quinolin-2-yl)amino)phenyl)acrylic acid, (E)-3-(3-(butyl(quinolin-2-yl)amino) phenyl)acrylic acid, C3 transferase, ZCL 278, Rhosin hydrochloride, ML 141, CASIN, p120 catenin, MLS000532223, and/or MLS000573151.
19. The method of any of embodiments 15-18, wherein the Rho GTPases include RhoA and/or Rac1.
20. The method of embodiment 19, wherein the compound that inhibits Rac1 includes EHT 1864, Rac1 Inhibitor W56, NSC 23766, EHop 016, 6-mercaptopurine (6-MP), and/or 6-thioguanosine-5'-tri phosphate (6-T-GTP).
21. The method of any of embodiments 15-20, wherein the compound that inhibits NOD2 includes from ponatinib, regorafenib, gefitinib, curcumin, a sesquiterpene lactone, a pseudopterosin, a polyunsaturated fatty acid, a benzimidazole diamide, and/or a hydrophenalene-chromium complex.

22. The method of any of embodiments 15-21, wherein the compound that inhibits NOD2 includes a sesquiterpene lactone selected from parthenolide and/or helenalin.

23. The method of any of embodiments 15-22, wherein the compound that inhibits NOD2 includes pseudopterosin A.

24. The method of any of embodiments 15-23, wherein the compound that inhibits NOD2 includes a polyunsaturated fatty acid selected from docosahexaenoic acid (DHA) and/or eicosapentaenoic acid (EPA).

25. The method of any of embodiments 15-24, wherein the compound that inhibits NOD2 includes a benzimidazole diamide selected from GSK669 and/or GSK717.

26. The method of any of embodiments 15-25, wherein the compound that inhibits miR29c includes a complementary interfering RNA sequence.

27. The method of any of embodiments 15-26, wherein the compound that inhibits miR29c includes SEQ ID NO: 12.

28. The method of any of embodiments 15-27, wherein the compound that inhibits miR29c includes a PPAR-γ agonist.

29. The method of embodiment 28, wherein the PPAR-γ agonist includes pioglitazone, 15-deoxy-delta-12,14-$PGJ_2$ and/or thiazolidinedione.

30. A composition including a therapeutically effective amount of a compound that inhibits Rho GTPases, NOD2, and/or miR29c wherein therapeutically effective promotes thymic regeneration.

31. The composition of embodiment 30, wherein the therapeutically effective promotes thymic regeneration by up-regulating IL-22, IL-23, and/or BMP4 within a subject.

32. The composition of embodiment 30 or 31, wherein the compound that inhibits Rho GTPases includes EHT 1864, Rac1 Inhibitor W56, NSC 23766, EHop 016, 6-mercaptopurine (6-MP), 6-thioguanosine-5'-triphosphate (6-T-GTP), isoflavones, (E)-3-(3-(ethyl(quinolin-2-yl)amino)phenyl)acrylic acid, (E)-3-(3-(butyl(quinolin-2-yl)amino)phenyl)acrylic acid, C3 transferase, ZCL 278, Rhosin hydrochloride, ML 141, CASIN, p120 catenin, MLS000532223, and/or MLS000573151.

33. The composition of any of embodiments 30-32, wherein the compound that inhibits Rho GTPases inhibits RhoA and/or Rac1.

34. The composition of embodiment 33, wherein the compound that inhibits Rac1 includes EHT 1864, Rac1 Inhibitor W56, NSC 23766, EHop 016, 6-mercaptopurine (6-MP), and/or 6-thioguanosine-5'-triphosphate (6-T-GTP).

35. The composition of any of embodiments 30-34, wherein the compound that inhibits NOD2 includes ponatinib, regorafenib, gefitinib, curcumin, a sesquiterpene lactone, a pseudopterosin, a polyunsaturated fatty acid, a benzimidazole diamide, and/or a hydrophenalene-chromium complex.

36. The composition of any of embodiments 30-35, wherein the compound that inhibits NOD2 includes a sesquiterpene lactone selected from parthenolide and/or helenalin.

37. The composition of any of embodiments 30-36, wherein the compound that inhibits NOD2 includes pseudopterosin A.

38. The composition of any of embodiments 30-37, wherein the compound that inhibits NOD2 includes a polyunsaturated fatty acid selected from docosahexaenoic acid (DHA) and/or eicosapentaenoic acid (EPA).

39. The composition of any of embodiments 30-38, wherein the compound that inhibits NOD2 includes a benzimidazole diamide selected from GSK669 and/or GSK717.

40. The composition of any of embodiments 30-39, wherein the compound that inhibits miR29c includes a complementary interfering RNA sequence.

41. The composition of any of embodiments 30-40, wherein the compound that inhibits miR29c includes SEQ ID NO: 12.

42. The composition of any of embodiments 30-41, wherein the compound that inhibits miR29c includes a PPAR-γ agonist.

43. The composition of embodiment 45, wherein the PPAR-γ agonist includes pioglitazone, 15-deoxy-delta-12,14-$PGJ_2$ and/or thiazolidinedione.

44. A method or composition according to any of embodiments 1-43, wherein inhibiting RhoA, Rac1, Rac2, and/or Rac3 up-regulates BMP4.

45. A method or composition according to any of embodiments 1-43, wherein inhibiting RhoA and/or Rac1 up-regulates IL-23 and/or BMP4.

46. A method or composition according to any of embodiments 1-43, wherein inhibiting NOD2 up-regulates IL-22, IL-23, and/or BMP4.

Variants of the sequences disclosed and referenced herein are also included. Variants of proteins can include those having one or more conservative amino acid substitutions or one or more non-conservative substitutions that do not alter the description of a protein's behavior according to an assay or test described herein to a statistically significant degree.

A "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gin); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

The nucleic acid sequences described herein are shown using standard letter abbreviations for nucleotide bases, as defined in 37 C.F.R. § 1.822. Only one strand of each nucleic acid sequence is shown, but the complementary strand is understood as included in embodiments where it would be appropriate.

As indicated elsewhere, variants of gene sequences can include codon optimized variants, sequence polymorphisms, splice variants, and/or mutations that do not affect the function of an encoded product to a statistically-significant degree. Of most importance to the current disclosure is that there be enough sequence complementarity to mediate targeted gene inhibition.

Variants of the protein and nucleic acid sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein and nucleic acid sequences described or disclosed herein.

"% sequence identity" refers to a relationship between two or more sequences, as determined by comparing the sequences. In the art, "identity" also means the degree of sequence relatedness between protein and nucleic acid sequences as determined by the match between strings of such sequences. "Identity" (often referred to as "similarity") can be readily calculated by known methods, including those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. "Default values" will mean any set of values or parameters, which originally load with the software when first initialized.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in the ability of an inhibitory composition disclosed herein to promote thymic regeneration according to an assay as depicted in relation to FIG. 3.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A method of promoting thymic regeneration in a subject in need thereof by administering a therapeutically effective amount of the Rac1 inhibitor EHT 1864 to the subject thereby promoting thymic regeneration in the subject.

2. A method of promoting thymic regeneration in a subject in need thereof comprising administering a therapeutically effective amount of a composition that inhibits Rho GTPases, NOD2, and/or miR29c to the subject, wherein the composition that inhibits RhoGTPases comprises (E)-3-(3-(ethyl(quinolin-2-yl)amino)phenyl)acrylic acid, (E)-3-(3-(butyl(quinolin-2-yl)amino)phenyl)acrylic acid, C3 transferase, ZCL 278, Rhosin hydrochloride, ML 141, CASIN, p120 catenin, MLS000532223, MLS000573151, EHT 1864, Rac1 Inhibitor W56, NSC 23766, EHop 016, 6-mercaptopurine (6-MP), and/or 6-thioguanosine-5'-triphosphate (6-T-GTP), thereby promoting thymic regeneration in the subject.

3. The method of claim 2, wherein the subject is in need of promoted thymic regeneration due to age, infection, and/or a cancer treatment.

4. The method of claim 2, wherein the compound that inhibits NOD2 comprises ponatinib, regorafenib, gefitinib, curcumin, a sesquiterpene lactone, a pseudopterosin, a polyunsaturated fatty acid, a benzimidazole diamide, and/or a hydrophenalene-chromium complex.

5. The method of claim 2, wherein the compound that inhibits NOD2 comprises a sesquiterpene lactone selected from parthenolide and/or helenalin.

6. The method of claim 2, wherein the compound that inhibits NOD2 comprises pseudopterosin A.

7. The method of claim 2, wherein the compound that inhibits NOD2 comprises a polyunsaturated fatty acid selected from docosahexaenoic acid (DHA) and/or eicosapentaenoic acid (EPA).

8. The method of claim 2, wherein the compound that inhibits NOD2 comprises a benzimidazole diamide selected from GSK669 and/or GSK717.

9. The method of claim 2, wherein the compound that inhibits miR29c comprises a complementary interfering RNA sequence.

10. The method of claim 2, wherein the compound that inhibits miR29c comprises SEQ ID NO: 12.

11. The method of claim 2, wherein the compound that inhibits miR29c comprises a PPAR-γ agonist.

12. The method of claim 11, wherein the PPAR-γ agonist comprises pioglitazone, 15-deoxy-delta-12,14-PGJ2 and/or thiazolidinedione.

13. A method of upregulating interleukin (IL)-22, IL-23, and/or bone morphogenetic protein 4 (BMP4) in a subject comprising administering a therapeutically effective amount of Rac1 inhibitor EHT 1864 to the subject thereby upregulating IL-22, IL-23, and/or BMP4 in the subject.

14. The method of claim 13, wherein the upregulating promotes thymic regeneration in the subject.

15. A method of upregulating IL-22, IL-23, and/or BMP4 in a subject in need thereof comprising administering a therapeutically effective amount of a composition that inhibits Rho GTPases, NOD2, and/or miR29c to the subject, wherein the composition that inhibits RhoGTPases comprises (E)-3-(3-(ethyl(quinolin-2-yl)amino)phenyl)acrylic acid, (E)-3-(3-(butyl(quinolin-2-yl)amino)phenyl)acrylic acid, C3 transferase, ZCL 278, Rhosin hydrochloride, ML 141, CASIN, p120 catenin, MLS000532223, MLS000573151, EHT 1864, Rac1 Inhibitor W56, NSC 23766, EHop 016, 6-mercaptopurine (6-MP), and/or 6-thioguanosine-5'-triphosphate (6-T-GTP), thereby upregulating IL-22, IL-23, and/or BMP4 in the subject.

16. The method of claim 15, wherein the upregulating promotes thymic regeneration in the subject.

17. The method of claim 15, wherein the subject has reduced thymic function due to age, infection, and/or a cancer treatment.

18. The method of claim 15, wherein the compound that inhibits NOD2 comprises from ponatinib, regorafenib, gefitinib, curcumin, a sesquiterpene lactone, a pseudopterosin, a polyunsaturated fatty acid, a benzimidazole diamide, and/or a hydrophenalene-chromium complex.

19. The method of claim 15, wherein the compound that inhibits NOD2 comprises a sesquiterpene lactone selected from parthenolide and/or helenalin.

20. The method of claim 15, wherein the compound that inhibits NOD2 comprises pseudopterosin A.

21. The method of claim 15, wherein the compound that inhibits NOD2 comprises a polyunsaturated fatty acid selected from docosahexaenoic acid (DHA) and/or eicosapentaenoic acid (EPA).

22. The method of claim 15, wherein the compound that inhibits NOD2 comprises a benzimidazole diamide selected from GSK669 and/or GSK717.

23. The method of claim 15, wherein the compound that inhibits miR29c comprises a complementary interfering RNA sequence.

24. The method of claim 15, wherein the compound that inhibits miR29c comprises SEQ ID NO: 12.

25. The method of claim 15, wherein the compound that inhibits miR29c comprises a PPAR-γ agonist.

26. The method of claim 25, wherein the PPAR-γ agonist comprises pioglitazone, 15-deoxy-delta-12,14-PGJ2 and/or thiazolidinedione.

27. The method of claim 2, wherein the subject has received pre-bone marrow transplantation conditioning, chemotherapy, radiotherapy, cisplatin, cyclophosphamide (CPA), Vinorelbine, nucleoside-based analogues, fractionated low-dose radiation, recombinant human IL-2 (rhIL-2), CP-31398 (N'-[2-[2-(4-methoxyphenyl)ethenyl]-4-quinazolmyl]-N,N-dimethyl-1,3-propanediamine dihydrochloride), synthetic retinoic acid analog, flavopiridol, E-4IB (ethyl-4-isothiocyanatobutanoate), 5-fluorouracil (5-FU), 5'-deoxy-5-fluorouridine (5'-DFUR), or cyclosporine A.

28. The method of claim 3, wherein the infection comprises Human Immunodeficiency Virus (HIV), hepatitis, subacute sclerosing panencephalitis, chronic papovavirus encephalitis, or Epstein-Barr virus infection.

29. The method of claim 2, further comprising administering keratinocyte growth factor (KGF), ghrelin, human growth hormone, and/or IL-22, and/or BMP4.

30. The method of claim 2, wherein thymic regeneration comprises an increase in T cells.

31. The method of claim 15, wherein the subject has received pre-bone marrow transplantation conditioning, chemotherapy, radiotherapy, cisplatin, cyclophosphamide (CPA), Vinorelbine, nucleoside-based analogues, fractionated low-dose radiation, recombinant human IL-2 (rhIL-2), CP-31398 (N'-[2-[2-(4-methoxyphenyl)ethenyl]-4-quinazolmyl]-N,N-dimethyl-1,3-propanediamine dihydrochloride), synthetic retinoic acid analog, flavopiridol, E-4IB (ethyl-4-isothiocyanatobutanoate), 5-fluorouracil (5-FU), 5'-deoxy-5-fluorouridine (5'-DFUR), or cyclosporine A.

32. The method of claim 17, wherein the infection comprises Human Immunodeficiency Virus (HIV), hepatitis, subacute sclerosing panencephalitis, chronic papovavirus encephalitis, or Epstein-Barr virus infection.

33. The method of claim 15, further comprising administering keratinocyte growth factor (KGF), ghrelin, human growth hormone, and/or IL-22, and/or BMP4.

34. The method of claim 15, wherein thymic regeneration comprises an increase in T cells.

* * * * *